United States Patent
On et al.

(10) Patent No.: US 9,621,781 B2
(45) Date of Patent: Apr. 11, 2017

(54) FOCUS CONTROL DEVICE, ENDOSCOPE SYSTEM, AND FOCUS CONTROL METHOD

(71) Applicant: OLYMPUS CORPORATION, Shibuya-ku, Tokyo (JP)

(72) Inventors: Seigo On, Hachioji (JP); Naoya Kuriyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 422 days.

(21) Appl. No.: 14/226,571

(22) Filed: Mar. 26, 2014

(65) Prior Publication Data

US 2014/0210972 A1 Jul. 31, 2014

Related U.S. Application Data

(63) Continuation of application No. PCT/JP2012/076158, filed on Oct. 10, 2012.

(30) Foreign Application Priority Data

Oct. 11, 2011 (JP) .................................. 2011-224204
Sep. 4, 2012 (JP) .................................. 2012-193932

(51) Int. Cl.
*H04N 5/232* (2006.01)
*G02B 7/36* (2006.01)
(Continued)

(52) U.S. Cl.
CPC ..... *H04N 5/23212* (2013.01); *A61B 1/00096* (2013.01); *A61B 1/00188* (2013.01);
(Continued)

(58) Field of Classification Search
CPC ............ H04N 5/23212; H04N 1/00328; H04N 5/23296
See application file for complete search history.

(56) References Cited

U.S. PATENT DOCUMENTS

2007/0257996 A1* 11/2007 Kurosawa ............. G06T 3/4015
348/240.99
2008/0024620 A1 1/2008 Yoshida et al.
(Continued)

FOREIGN PATENT DOCUMENTS

JP 11-023949 A 1/1999
JP 2002-258164 A 9/2002
(Continued)

OTHER PUBLICATIONS

Extended European Search Report dated Jun. 10, 2015, issued in counterpart European Application No. 12839972.2.
(Continued)

*Primary Examiner* — Obafemi Sosanya
(74) *Attorney, Agent, or Firm* — Holtz, Holtz & Volek PC

(57) ABSTRACT

The focus control device includes a focus control section that controls an imaging optical system that is configured so that an in-focus object plane position is changed when an imaging magnification is changed, an image acquisition section that acquires a plurality of images captured through the imaging optical system at a different imaging magnification, and a change-in-magnification detection section that detects a change in magnification that is at least one of a change in the imaging magnification and a change in size of an object within an image among the plurality of images, the focus control section driving the imaging optical system based on an AF evaluation value that indicates the focus state of the imaging optical system and calculated based on the image and the change in magnification to control focus of the imaging optical system.

26 Claims, 25 Drawing Sheets

(51) Int. Cl.
*A61B 1/00* (2006.01)
*A61B 1/045* (2006.01)
*G02B 23/24* (2006.01)
*H04N 5/225* (2006.01)

(52) U.S. Cl.
CPC .............. *A61B 1/045* (2013.01); *G02B 7/36* (2013.01); *G02B 23/2438* (2013.01); *G02B 23/2469* (2013.01); *G02B 23/2484* (2013.01); *H04N 5/2256* (2013.01); *H04N 2005/2255* (2013.01)

(56) References Cited

U.S. PATENT DOCUMENTS

| | | | |
|---|---|---|---|
| 2008/0284900 A1 | 11/2008 | Abe | |
| 2011/0249150 A1* | 10/2011 | Shintani | H04N 5/23212 348/240.3 |
| 2012/0182462 A1* | 7/2012 | Hamada | H04N 5/23212 348/352 |

FOREIGN PATENT DOCUMENTS

| | | |
|---|---|---|
| JP | 2003069881 A | 3/2003 |
| JP | 2005-043792 A | 2/2005 |
| JP | 2006-215105 A | 8/2006 |
| JP | 2006-343496 A | 12/2006 |
| JP | 2007133265 A | 5/2007 |
| JP | 2008-035332 A | 2/2008 |
| JP | 2008-276214 A | 11/2008 |

OTHER PUBLICATIONS

International Search Report (ISR) dated Jan. 22, 2013 (and English translation thereof) issued in International Application No. PCT/JP2012/076158.

"Rotation Measurements using Rotation Invariant Phase-only correlation", The Journal of the Institute of Image Information and Television Engineers, 22 (45), Sep. 14, 1998, pp. 55-60.

David G. Lowe: "Distinctive image features from scale-invariant keypoints", Journal of Computer Vision, 60, 2, 2004, pp. 91-110.

Fischler M.A., et al.: "Random sample consensus: A paradigm for model fitting with applications to image analysis and automated cartography", Commun. ACM, No. 24, vol. 6, Jun. 1981, pp. 381-395.

* cited by examiner

ENDOSCOPIC IMAGE
(AT START OF AF OPERATION)

ENDOSCOPIC IMAGE
(CUMULATIVE MAGNIFICATION < 1.0)

SCALED IMAGE
(IMAGE SCALE FACTOR > 1.0)

ENDOSCOPIC IMAGE
(CUMULATIVE MAGNIFICATION > 1.0)

SCALED IMAGE
(IMAGE SCALE FACTOR < 1.0)

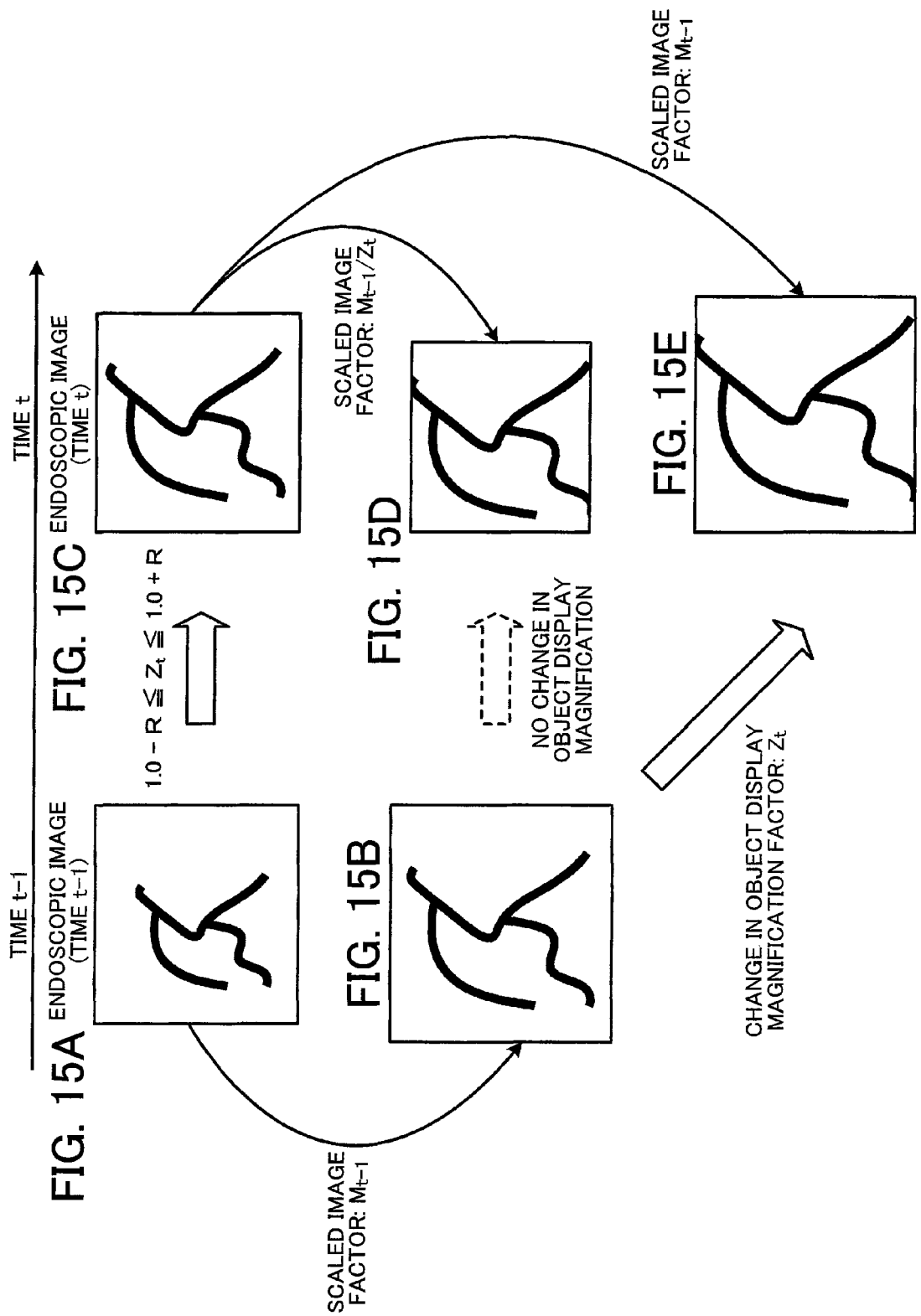

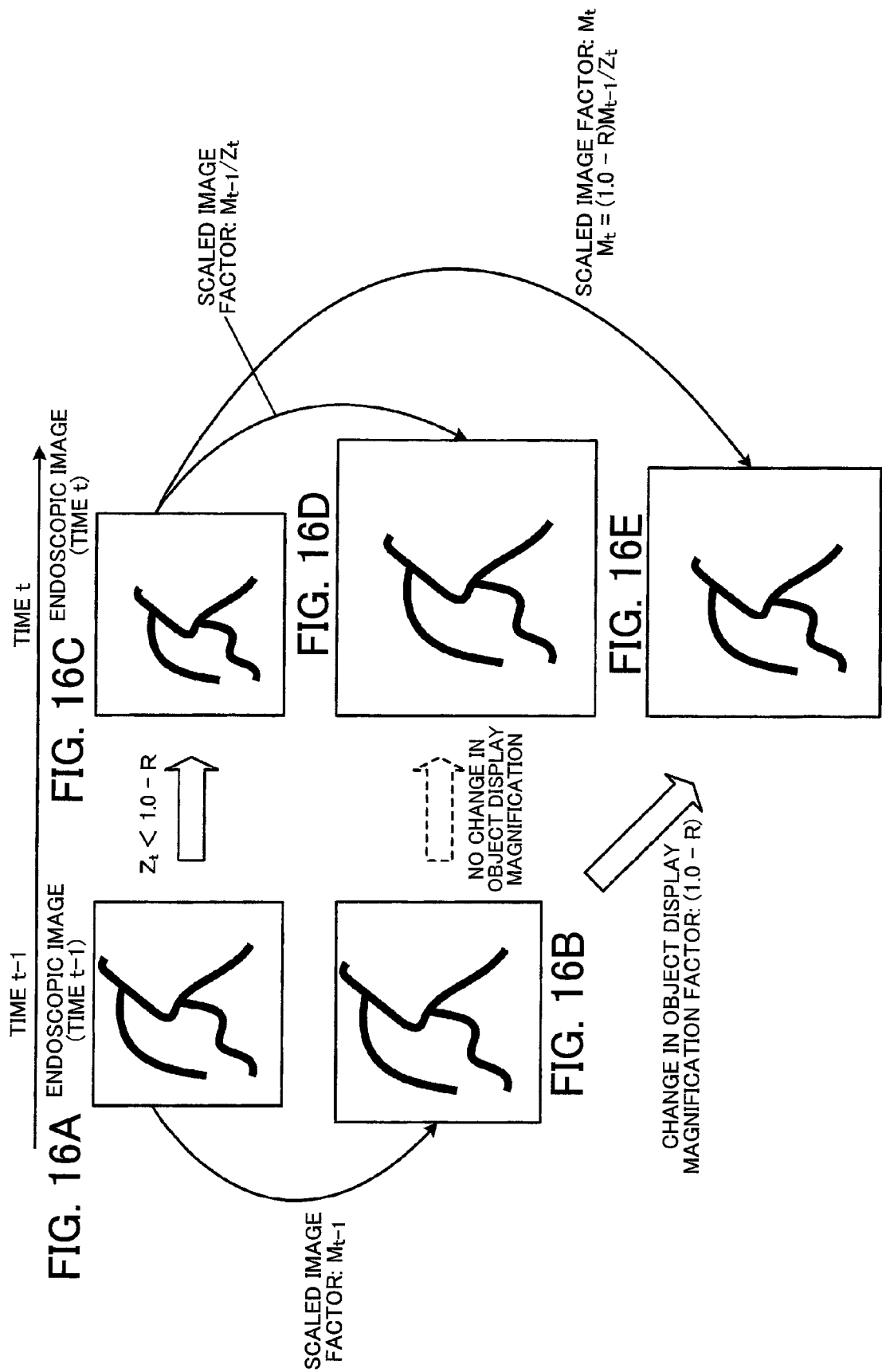

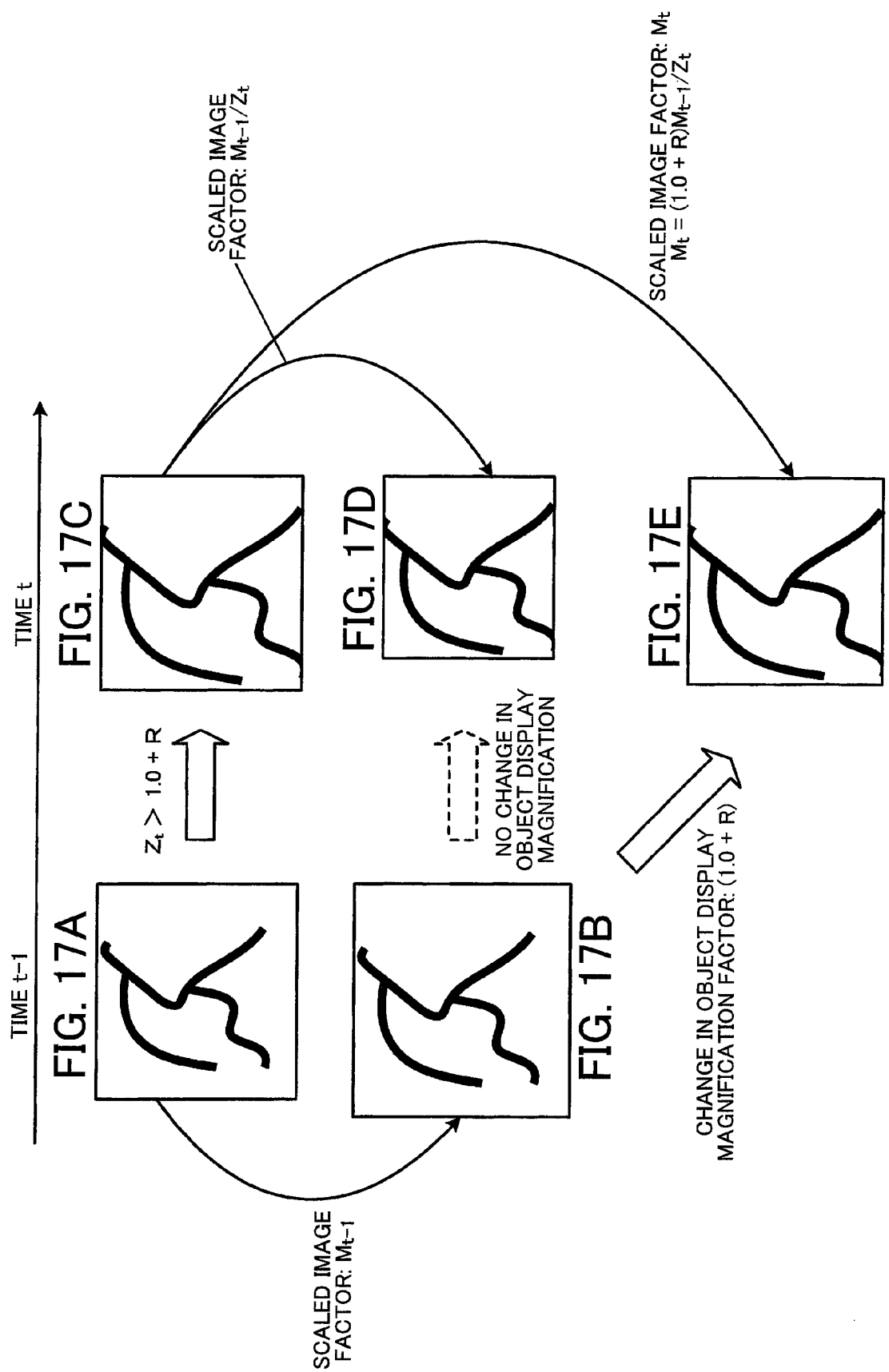

FOCUS CONTROL DEVICE, ENDOSCOPE SYSTEM, AND FOCUS CONTROL METHOD

CROSS REFERENCE TO RELATED APPLICATION

This application is a continuation of International Patent Application No. PCT/JP2012/076158, having an international filing date of Oct. 10, 2012, which designated the United States, the entirety of which is incorporated herein by reference. Japanese Patent Application No. 2011-224204 filed on Oct. 11, 2011 and Japanese Patent Application No. 2012-193932 filed on Sep. 4, 2012 are also incorporated herein by reference in its entirety.

BACKGROUND

The present invention relates to a focus control device, an endoscope system, a focus control method, and the like.

An endoscope system has been widely used that applies illumination light to tissue inside a body cavity, and allows the user to perform a diagnosis/procedure using image signals generated based on reflected light from the tissue. Since an endoscope optical system is normally designed to achieve deep focus with a deep depth of field, an image in which the object is in focus from the far point to the near point can be acquired during normal observation.

However, since the depth of field becomes shallow during zoom observation, the object may frequently become out of focus (defocused). In this case, since the user must perform a manual focus operation in order to observe the object using an in-focus endoscopic image, the burden imposed on the user increases.

An autofocus (AF) function may be introduced to solve the problem in which it is difficult to bring the object into focus during zoom observation. The user need not perform the manual focus operation as a result of introducing the AF function. For example, the endoscope system disclosed in JP-A-2002-258164 perform an AF operation during normal observation and zoom observation.

The AF operation (function) may be implemented using the optical system configuration illustrated in FIG. 19A or 19B. The configuration (single-lens drive configuration) illustrated in FIG. 19A is designed so that the in-focus object plane position is controlled by driving the zoom lens. Therefore, the magnification also changes when the in-focus object plane position is changed. The configuration (dual-lens drive configuration) illustrated in FIG. 19B is designed so that the zoom lens and the focus lens can be driven, and has an advantage in that the magnification and the in-focus object plane position can be controlled independently. However, the dual-lens drive configuration is complex as compared with the single-lens drive configuration. Therefore, it is difficult to implement the dual-lens drive configuration as compared with the single-lens drive configuration, and the diameter of the endoscope necessarily increases when the dual-lens drive configuration is incorporated in the endoscope.

Accordingly, it is desirable to employ the single-lens drive configuration illustrated in FIG. 19A for the endoscopic scope.

SUMMARY

According to one aspect of the invention, there is provided a focus control device comprising:

a focus control section that controls an imaging optical system that is configured so that an in-focus object plane position is changed when an imaging magnification is changed;

an image acquisition section that acquires a plurality of images captured through the imaging optical system at a different imaging magnification;

a change-in-magnification detection section that detects a change in magnification, the change in magnification being at least one of a change in the imaging magnification and a change in size of an object within an image among the plurality of images; and an image scaling section that subjects the image to an image scaling process based on the change in magnification to acquire a scaled image, the focus control section calculating an autofocus (AF) evaluation value that indicates a focus state of the imaging optical system based on the image and the change in magnification, and driving the imaging optical system based on the calculated AF evaluation value to control focus of the imaging optical system, and the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

According to another aspect of the invention, there is provided an endoscope system comprising:

a focus control section that controls an imaging optical system that is configured so that an in-focus object plane position is changed when an imaging magnification is changed;

an image acquisition section that acquires a plurality of images captured through the imaging optical system at a different imaging magnification;

a change-in-magnification detection section that detects a change in magnification, the change in magnification being at least one of a change in the imaging magnification and a change in size of an object within an image among the plurality of images; and an image scaling section that subjects the image to an image scaling process based on the change in magnification to acquire a scaled image, the focus control section calculating an autofocus (AF) evaluation value that indicates a focus state of the imaging optical system based on the image and the change in magnification, and driving the imaging optical system based on the calculated AF evaluation value to control focus of the imaging optical system, and the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

According to another aspect of the invention, there is provided a focus control method that controls an imaging optical system that is configured so that an in-focus object plane position is changed when an imaging magnification is changed, the focus control method comprising:

acquiring a plurality of images captured through the imaging optical system at a different imaging magnification;

detecting a change in magnification that is at least one of a change in the imaging magnification and a change in size of an object within an image among the plurality of images;

subjecting the image to an image scaling process based on the change in magnification to acquire a scaled image;

calculating an autofocus (AF) evaluation value that indicates a focus state of the imaging optical system based on the acquired image and the change in magnification, and driving the imaging optical system based on the calculated AF evaluation value to control focus of the imaging optical system; and calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

BRIEF DESCRIPTION I/F THE DRAWINGS

FIGS. 15A to 15E illustrate an example of an endoscopic image and a scaled image when a change in magnification is within the range of an allowable scale factor.

FIGS. 16A to 16E illustrate an example of an endoscopic image and a scaled image when a change in magnification is smaller than an allowable scale factor.

FIGS. 17A to 17E illustrate an example of an endoscopic image and a scaled image when a change in magnification is larger than an allowable scale factor.

DESCRIPTION I/F EXEMPLARY EMBODIMENTS

Figure 1:
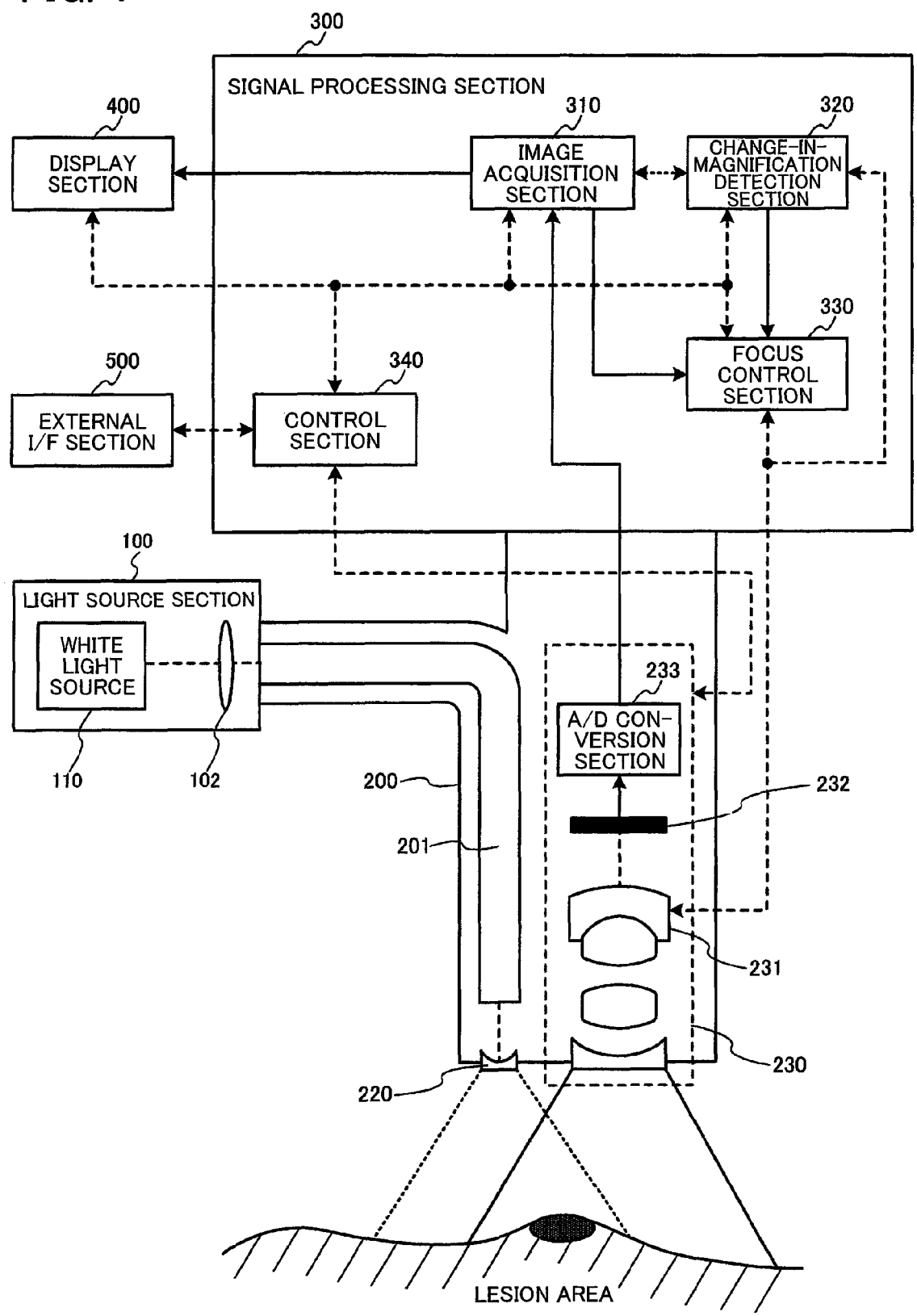
FIG. 1 illustrates a configuration example of a focus control device according to a first embodiment and an endoscope system including the same.

According to one embodiment of the invention, there is provided a focus control device comprising: a focus control section that controls an imaging optical system that is configured so that an in-focus object plane position is changed when an imaging magnification is changed; an image acquisition section that acquires a plurality of images captured through the imaging optical system at a different imaging magnification; a change-in-magnification detection section that detects a change in magnification, the change in magnification being at least one of a change in the imaging magnification and a change in size of an object within an image among the plurality of images; and an image scaling section that subjects the image to an image scaling process based on the change in magnification to acquire a scaled image, the focus control section calculating an autofocus (AF) evaluation value that indicates a focus state of the imaging optical system based on the image and the change in magnification, and driving the imaging optical system based on the calculated AF evaluation value to control focus of the imaging optical system, and the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

According to one embodiment of the invention, the imaging optical system is configured so that the in-focus object plane position is changed when the imaging magnification is changed. The change in magnification that is at least one of the change in the imaging magnification and the change in the size of the object within the image is detected, and the AF evaluation value is calculated based on the detected change in magnification. This makes it possible to suppress the effects of a change in the imaging magnification along with a change in the in-focus object plane position when calculating the AF evaluation value at a different in-focus object plane position, and stably calculate the AF evaluation value, for example.

According to another embodiment of the invention, there is provided an endoscope system comprising: a focus control section that controls an imaging optical system that is configured so that an in-focus object plane position is changed when an imaging magnification is changed; an image acquisition section that acquires a plurality of images captured through the imaging optical system at a different imaging magnification; a change-in-magnification detection section that detects a change in magnification, the change in magnification being at least one of a change in the imaging magnification and a change in size of an object within an image among the plurality of images; and an image scaling section that subjects the image to an image scaling process based on the change in magnification to acquire a scaled image, the focus control section calculating an autofocus (AF) evaluation value that indicates a focus state of the imaging optical system based on the image and the change in magnification, and driving the imaging optical system based on the calculated AF evaluation value to control focus of the imaging optical system, and the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

According to another embodiment of the invention, there is provided a focus control method that controls an imaging optical system that is configured so that an in-focus object plane position is changed when an imaging magnification is changed, the focus control method comprising: acquiring a plurality of images captured through the imaging optical system at a different imaging magnification; detecting a change in magnification that is at least one of a change in the imaging magnification and a change in size of an object within an image among the plurality of images; subjecting the image to an image scaling process based on the change in magnification to acquire a scaled image; calculating an autofocus (AF) evaluation value that indicates a focus state of the imaging optical system based on the acquired image and the change in magnification, and driving the imaging optical system based on the calculated AF evaluation value to control focus of the imaging optical system; and calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

Figure 19A:
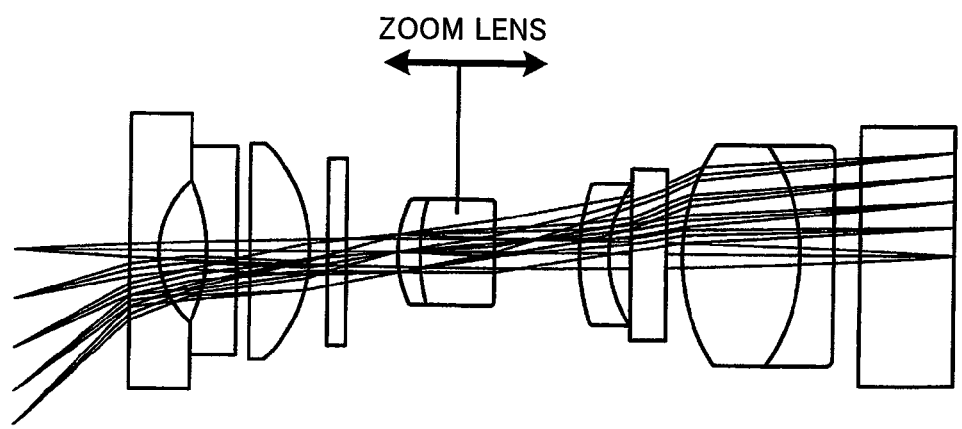
FIG. 19A illustrates an example of a single-lens drive configuration.
Figure 19B:
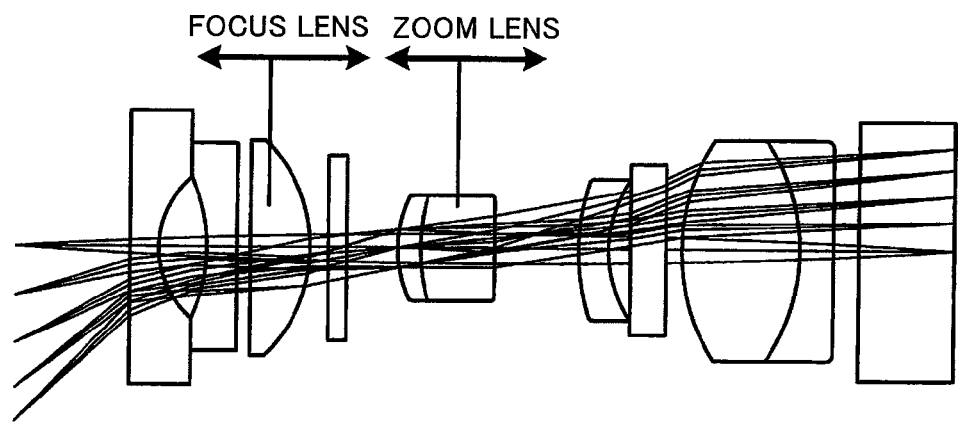
FIG. 19B illustrates an example of a dual-lens drive configuration.

A method employed in connection with several exemplary embodiments of the invention is described below. The single-lens drive configuration (see FIG. 19A) is designed so that the in-focus object plane position is changed by moving the zoom lens. Specifically, the imaging magnification changes as a result of changing (moving) the in-focus object plane position. Therefore, when implementing the AF (autofocus) operation using the single-lens drive configuration, a problem may occur when calculating the AF evaluation value (e.g., contrast value) used for the AF operation.

The term "in-focus object plane position" used herein refers to the position of the object (object point) relative to a reference position when a system including the object, the imaging optical system, the image plane, and the like is in an in-focus state. Specifically, when the image plane is set to a given position, and the imaging optical system is set to a given state, the in-focus object plane position refers to the position of the object when the image formed in the image plane by the imaging optical system is in focus. A focus control device (or endoscope system) and the like according to several exemplary embodiments of the invention are designed on the assumption that the image plane coincides with the plane of an image sensor included in an imaging section, and the in-focus object plane position can be determined by determining the state of the optical system when the plane of the image sensor is fixed.

When implementing the contrast AF operation, the contrast values may be calculated while changing the in-focus object plane position, and the relationship between a plurality of AF evaluation values may be calculated to determine the maximum value among the calculated contrast values. When using the single-lens drive configuration, however, the imaging magnification is changed when the in-focus object plane position is changed. Therefore, since the magnification of the object differs between the image used to calculate the AF evaluation value at a certain timing and the image used to calculate the AF evaluation value at another timing, it may be difficult to stably calculate the AF evaluation value. For example, when the imaging magnification has increased (i.e., when the image has been magnified) during the AF operation, the high-frequency component included in the image is shifted to the low-frequency side (i.e., the edge is rounded), whereby a difference in AF evaluation value calculation conditions occurs. In this case, it may be difficult to appropriately determine the AF evaluation value, and the AF operation may be hindered.

In order to solve the above problems, several embodiments of the invention propose an AF evaluation value calculation method that compensates for a change in magnification (change-in-magnification information). More specifically, several embodiments of the invention propose three methods. In a first embodiment, the frequency characteristics of a filter used to calculate the AF evaluation value are changed based on the change in magnification. In a second embodiment, the size of an evaluation area that indicates the range of pixels used to calculate the AF evaluation value is changed based on the change in magnification. In a third embodiment, an image is subjected to a scaling process based on the change in magnification, and the AF evaluation value is calculated using the resulting scaled image.

The change in magnification may be acquired in two ways. In the first embodiment, the change in magnification is acquired based on control information (e.g., a lens control signal relating to the position of the zoom lens) from an imaging optical system. In the second embodiment, the change in magnification is acquired based on the size of the object within the captured image. Note that the change in magnification acquired based on the control information is information that indicates a change in imaging magnification, and the change in magnification acquired based on the size of the object within the image is information that indicates a change in imaging magnification and a change in relative distance between the object and the imaging optical system.

In the first embodiment, a combination of the filtering process and the lens control signal is used to implement the AF evaluation value calculation method and the change-in-magnification detection method. In the second embodiment, a combination of the evaluation area and the size of the object is used to implement the AF evaluation value calculation method and the change-in-magnification detection method. Note that the combination of the AF evaluation value calculation method and the change-in-magnification detection method is not limited thereto. The three AF evaluation value calculation methods and the two change-in-magnification detection methods may be combined in an arbitrary manner. The change in magnification based on the lens control signal and the change in magnification based on the size of the object may be acquired in combination. This is advantageous when using the scaling process as the AF evaluation value calculation method. The details thereof are described later in connection with the third embodiment and a modification thereof.

When the imaging magnification changes due to wobbling of the zoom lens when calculating the AF evaluation value, the magnification (angle of view) of the display image presented to the user (doctor) frequently changes. However, a frequent change in angle of view of the display image is stressful for the doctor when performing diagnosis based on the display image, and may hinder an appropriate diagnosis. In order to deal with the above problem, a display image that is easy to observe may be generated and displayed by subjecting the captured image to an appropriate scaling process. A specific method is described later in connection with the third embodiment and a fourth embodiment. In the fourth embodiment, an arbitrary method among the above AF evaluation value calculation methods can be used.

The following description is mainly given on the assumption that the ratio of the imaging magnifications or the sizes of the object at adjacent two timings is the change in magnification Z, and the cumulative magnification A that is a direct product of the change in magnification Z corresponds to the ratio of the imaging magnifications or the like at a given two timings (i.e., adjacent timings or non-adjacent timings). Note that the change in magnification Z and the cumulative magnification A differ in calculation method, but similarly indicate the change in imaging magnification or the like between two different timings, and have substantially the same meaning. Accordingly, the cumulative magnification A is included within the term "change in magnification" in a broad sense. The change in magnification Z and the cumulative magnification A are selectively used where appropriate, but may be interchangeably used when it is difficult (or unnecessary) to distinguish the change in magnification Z and the cumulative magnification A.

2. First Embodiment

An endoscope system (endoscope apparatus) that includes a focus control device according to the first embodiment is described below with reference to FIG. 1. The endoscope system includes a light source section 100, an insertion section 200, a signal processing section 300, a display section 400, and an external I/F section 500.

The light source section 100 includes a white light source 110 and a condenser lens 120. The white light source 110 emits white light. The condenser lens 120 focuses the white light emitted from the white light source 110 on a light guide fiber 210 (described below).

Figure 2:
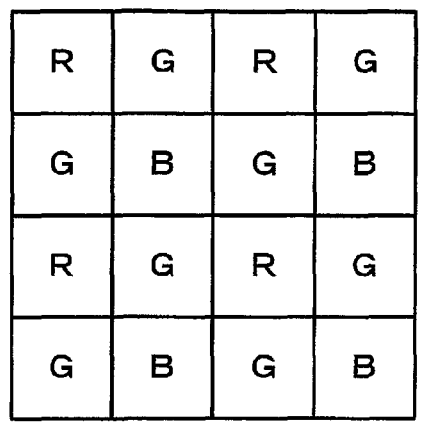
FIG. 2 illustrates a configuration example of an image sensor.

The insertion section 200 is formed to be elongated and flexible so that the insertion section 200 can be inserted into a body cavity, for example. The insertion section 200 includes the light guide fiber 210, an illumination lens 220, and an imaging section 230. The light guide fiber 210 guides the light focused by the light source section 100 to the end of the insertion section 200. The illumination lens 220 diffuses the light guided by the light guide fiber 210, and applies the diffused light to an observation target. The imaging section 230 includes an objective lens 231, an image sensor 232, and an A/D conversion section 233. The objective lens 231 focuses the reflected light from the observation target on the image sensor 232. The objective lens 230 also has a function of changing the magnification and the in-focus object plane position at the same time. The image sensor 232 outputs analog signals based on the detected reflected light to the A/D conversion section 233. The A/D conversion section 233 converts the analog signals output from the image sensor 232 into digital signals, and outputs the digital signals to the signal processing section 300 as a RAW image based on a control signal output from a control section 340 (described below). The image sensor 232 has a primary color Bayer array, and the image acquired by the image sensor 232 is a primary color Bayer image. As illustrated in FIG. 2, the primary color Bayer image is an image in which each pixel has an R, G, or B signal in a staggered pattern.

The signal processing section 300 includes an image acquisition section 310, a change-in-magnification detection section 320, a focus control section 330, and the control section 340. The RAW image output from the imaging section 230 is output to the image acquisition section 310. The image acquisition section 310 is connected to the focus control section 330 and the display section 400. The change-in-magnification detection section 320 is connected to the focus control section 330. The focus control section 330 is connected to the objective lens 231, and controls the magnification and the in-focus object plane position by controlling the objective lens 231 using a lens control signal. The lens control signal is also output to the change-in-magnification detection section 320. The control section 340 is bidirectionally connected to the imaging section 230, the change-in-magnification detection section 320, the focus control section 330, the image acquisition section 310, the display section 400, and the external I/F section 500, and controls the imaging section 230, the change-in-magnification detection section 320, the focus control section 330, the image acquisition section 310, the display section 400, and the external I/F section 500 using a control signal. The control signal includes an AF trigger signal that indicates the start/end of an autofocus (AF) operation (function) that automatically brings the object into focus. Note that each element connected to the control section 340 detects the start/end of the AF operation based on the control signal, for example.

The image acquisition section 310 performs image processing (e.g., white balance process and demosaicing process) on the RAW image output from the imaging section 230 to acquire an endoscopic image. The image acquisition section 310 outputs the acquired endoscopic image to the focus control section 330 and the display section 400. The endoscopic image is an RGB color image.

The change-in-magnification detection section 320 detects a temporal change in magnification of the objective lens 231 based on the lens control signal output from the focus control section 330 (described below). For example, when the magnification of the objective lens 231 at a time t (current time) is zt, and the magnification of the objective lens 231 at a time t−1 is zt−1, the change-in-magnification detection section 320 outputs a value Zt (=zt/zt−1) to the focus control section 330 as the change in magnification. Note that the time t and the time t−1 refer to a time at which the control signal is output to the change-in-magnification detection section 320, and the time t−1 refers to a time at which the control signal was output to the change-in-magnification detection section 320 immediately before the time t.

When the focus control section 330 has detected the start of the AF operation based on the control signal, the focus control section 330 controls the in-focus object plane position by controlling the objective lens 231 based on the endoscopic image output from the image acquisition section 310 and the change in magnification output from the change-in-magnification detection section 320. In the first embodiment, the expression "controls the in-focus object plane position" is used for convenience of explanation although the magnification also changes when the in-focus object plane position is changed.

A specific configuration of the focus control section 330 is described below with reference to FIG. 3. The focus control section 330 includes a filter selection section 331, a contrast value calculation section 332, and a lens control section 333. The endoscopic image output from the image acquisition section 310 is output to the contrast value calculation section 332. The change in magnification output from the change-in-magnification detection section 320 is output to the filter selection section 331. The filter selection section 331 is connected to the contrast value calculation section 332. The contrast value calculation section 332 is connected to the lens control section 333. The lens control section 333 is connected to the objective lens 231, and outputs the lens control signal to control the objective lens 231. The lens control signal is also output to the change-in-magnification detection section 320.

Figure 4:
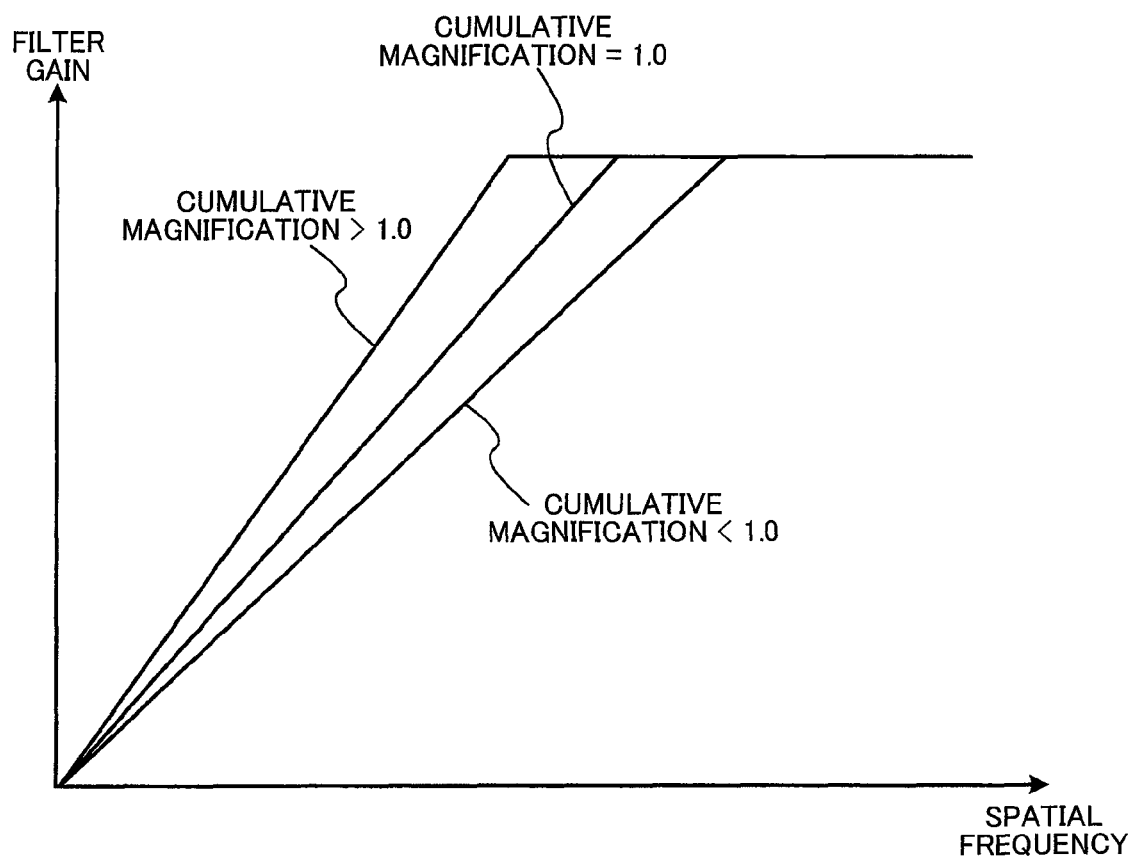
FIG. 4 is a view illustrating a method that changes filter frequency characteristics corresponding to a change in magnification.

The filter selection section 331 selects a filter that is used to calculate the contrast value from a given filter group based on the change in magnification output from the change-in-magnification detection section 320. The filter is a known high-pass filter. The following description is given on the assumption that the filter group includes three filters for convenience of explanation. When the focus control section 330 has detected the start of the AF operation based on the control signal, the filter selection section 331 calculates the cumulative magnification using the following expression (1).

$$A_t = \prod_s^t Z_i \quad (1)$$

where, t is the current time, At is the cumulative magnification at the current time, s is the start time of the AF operation, i is an index that indicates time, and Z is the change in magnification (change-in-magnification value). Specifically, the cumulative magnification is a direct product of the change in magnification from the start of the AF operation to the current time. A high-pass filter selection process based on the cumulative magnification is described below with reference to FIG. 4. FIG. 4 illustrates the frequency characteristics of a high-pass filter. When the cumulative magnification is larger than 1.0 (i.e., when the magnification is higher than that at the start of the AF operation), the filter selection section 331 selects a high-pass filter that allows a signal having a lower frequency to pass through as compared with that used at the start of the AF operation. When the cumulative magnification is smaller than 1.0 (i.e., when the magnification is lower than that at the start of the AF operation), the filter selection section 331 selects a high-pass filter that allows a signal having a higher frequency to pass through as compared with that used at the start of the AF operation. Although an example in which the filter group includes three filters has been described above, the filter group may include more than three filters. In such a case, a high-pass filter that allows a signal having a lower or higher frequency to pass through is selected as the cumulative magnification increases or decreases. The frequency characteristics of a given high-pass filter may be changed based on the cumulative magnification. In this case, a filter is designed to have the frequency characteristics represented by the following expression (2).

$$G_t(u) = G_o(A_t \times u) \quad (2)$$

where, Gt(u) is the frequency characteristics of the filter at the time t, u is the spatial frequency, and G0(u) is the frequency characteristics of a given filter.

Although an example in which a high-pass filter is used as the filter has been described above, a band-pass filter may be used as the filter. In this case, the filter selection section 331 selects a band-pass filter that allows a signal having a lower frequency to pass through as compared with that used at the start of the AF operation when the magnification is higher than that at the start of the AF operation, and selects a band-pass filter that allows a signal having a higher frequency to pass through as compared with that used at the start of the AF operation when the magnification is lower than that at the start of the AF operation.

The contrast value calculation section 332 performs a filtering process on the endoscopic image output from the image acquisition section 310 using the filter selected by the filter selection section 331 to calculate the contrast value. The contrast value refers to the sum of the pixel values of the endoscopic image subjected to the filtering process within a rectangular area that has a given size and is situated at the center of the endoscopic image. The contrast value is calculated by performing the filtering process on only the G signals of the endoscopic image. Specifically, since the G signal shows the largest local change in pixel value in a body cavity that is the main object within the endoscopic image, the G signal is suitably used to calculate the contrast value. The calculated contrast value is output to the lens control section 333. Although an example in which the contrast value is calculated by performing the filtering process on only the G signals has been described above, the contrast value may be calculated by performing the filtering process on all of the RGB signals on a channel basis, and calculating the sum of the values calculated for the RGB signals.

The lens control section 333 outputs the lens control signal that controls the objective lens 231 based on the contrast value output from the contrast value calculation section 332. A specific focus control method based on the contrast value is known as an AF technique, and detailed description thereof is omitted. The lens control signal is output to the objective lens 231 and the change-in-magnification detection section 320.

The display section 400 displays (outputs) the endoscopic image output from the image acquisition section 310 on an image display device (e.g., endoscope monitor).

The external I/F section 500 is an interface that allows the user to perform an input operation or the like on the focus control device. The external I/F section 500 includes a power switch (power ON/OFF switch), a shutter button (imaging operation start button), a mode (e.g., imaging mode) switch button, an AF button for stating the AF operation that automatically brings the object into focus, and the like.

According to one aspect of the invention, the endoscopic image is acquired through the endoscopic imaging optical system that is configured so that the magnification and the in-focus object plane position are changed in synchronization. A change in magnification of the endoscopic imaging optical system is detected from the control signal output from the endoscopic imaging optical system. The frequency characteristics of the high-pass filter are selected based on the detected change in magnification. The filtering process is performed on the endoscopic image using the high-pass filter to calculate the contrast value. The AF operation (function) is implemented by controlling the imaging optical system so that the calculated contrast value becomes a maximum. The AF operation can be stably performed corresponding to the change in magnification by calculating the contrast value using the filter having appropriate frequency characteristics corresponding to the change in magnification.

According to the first embodiment, the focus control device includes the focus control section 330 that drives (controls) the imaging optical system, the image acquisition section 310 that acquires a plurality of images captured through the imaging optical system at a different imaging magnification, and the change-in-magnification detection section 320 that detects a change in magnification (see FIG. 1). The focus control section 330 calculates the AF evaluation value that indicates the focus state of the imaging optical system based on the image acquired by the image acquisition section 310 and the change in magnification detected by the image and change-in-magnification detection section 320, and drives the imaging optical system based on the AF evaluation value to control the focus of the imaging optical system.

The imaging optical system is configured so that the in-focus object plane position is changed when the imaging magnification is changed. Specifically, the imaging optical system has the single-lens drive configuration illustrated in FIG. 19A. The term "change in magnification" refers to at least one of a change in imaging magnification and a change in size of the object within the image. For example, when the imaging magnification has changed from 2 to 3, the degree of change in the imaging magnification (ratio (3/2=1.5) or difference (3−2=1)) is taken as the change in magnification. For example, when the distance between two points of the object has changed from 10 pixels to 20 pixels within the image, the degree of change in size of the object (ratio (20/10=2) or difference (20−10=10)) is taken as the change in magnification. The term "change in magnification" in a broad sense is not limited to a ratio and a difference, but may be another piece of information (change-in-magnification information) that indicates the degree of change in imaging magnification or the like. Note that the term "change in magnification" in a narrow sense refers to a ratio. The term "AF evaluation value" refers to the evaluation target value when implementing the AF operation. For example, the AF evaluation value may be the contrast value used for the contrast AF operation.

According to the above configuration, since the AF evaluation value can be appropriately calculated even when using the single-lens drive configuration, it is possible to appropriately implement the AF operation. A plurality of AF evaluation values may be acquired at a plurality of timings that differ in the in-focus object plane position, and compared in the same manner as the contrast value used for the contrast AF operation. However, since the imaging magnification is changed when the in-focus object plane position is changed when using the single-lens drive configuration, the AF evaluation value calculation conditions change. Specifically, the high-frequency component of the image is shifted to the low-frequency side when the imaging magnification increases (i.e., the size enlargement process is performed). A change in the frequency component of the image affects the AF evaluation value (e.g., the high-frequency component of the image is used as the contrast value). According to the first embodiment, a process (i.e., a process that compensates for the effects of a change in magnification) based on a change in magnification (e.g., a change in imaging magnification) is performed when calculating the AF evaluation value from the image. Since the AF evaluation value can be stably calculated by employing the above configuration, it is possible to appropriately implement the AF operation.

Figure 3:
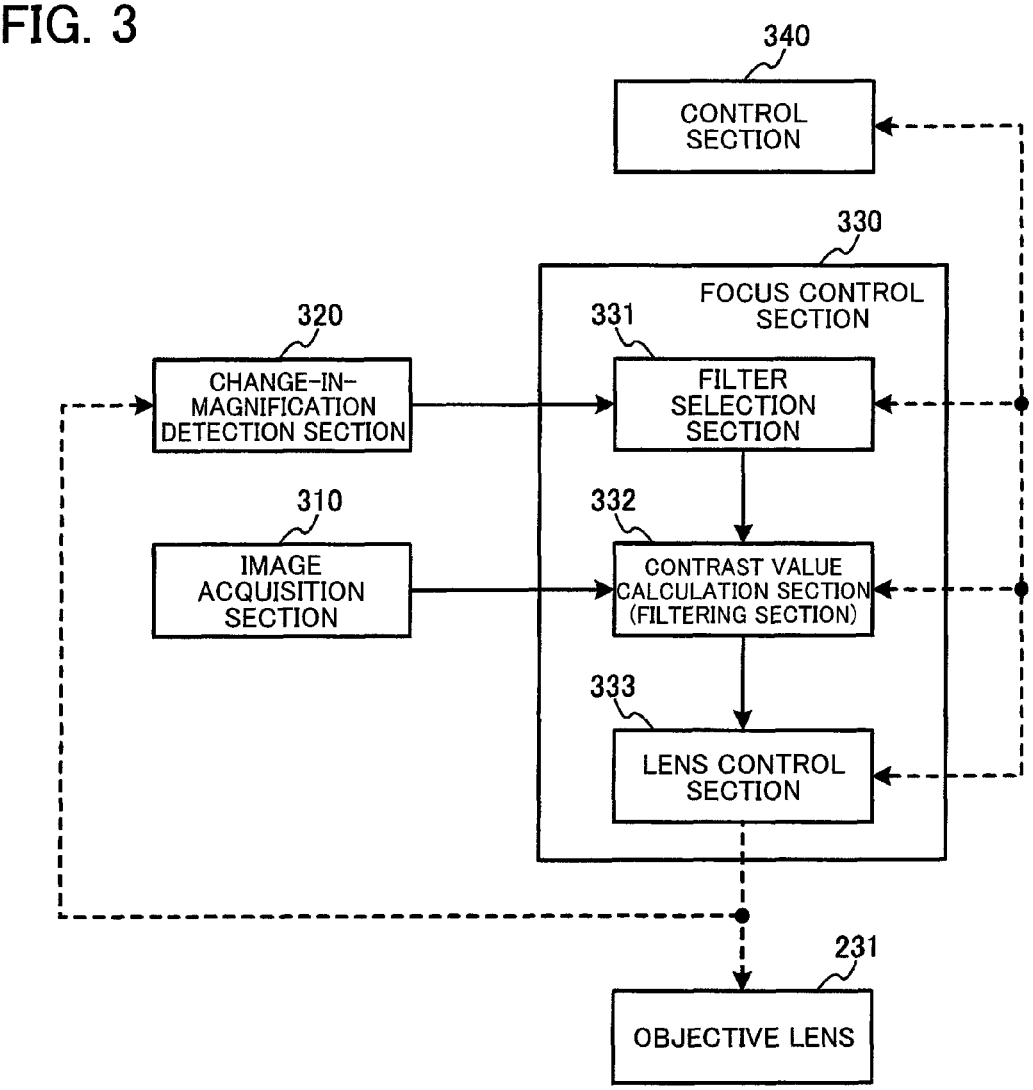
FIG. 3 illustrates a configuration example of a focus control section according to the first embodiment.

The focus control section 330 may include a filtering section (corresponding to the contrast value calculation section 332 illustrated in FIG. 3) that performs a filtering process on the image, the filtering process using a filter having frequency characteristics corresponding to the change in magnification (i.e., the filter selected by the filter selection section 331).

The above configuration makes it possible to change the frequency characteristics of the filter used to calculate the AF evaluation value based on the change in magnification. The frequency characteristics of the image change when the magnification is changed (see above). Therefore, when the frequency characteristics of the filter are constant, a signal component that can pass through the filter before the magnification is changed may not pass through the filter after the magnification has been changed even when the focus state is constant. Since a signal component (signal value) that passes through the filter is almost identical when the focus state is constant, it is necessary to change the filter characteristics corresponding to a change in frequency component of the image due to the change in magnification.

The filtering section may perform the filtering process using a high-pass filter having a relatively low cut-off frequency when the change in magnification is relatively large. The filtering section may perform the filtering process using a high-pass filter having a relatively high cut-off frequency when the change in magnification is relatively small.

Note that the ratio of two imaging magnifications is used as the degree of change in imaging magnification (or the degree of change in size of the object) (i.e., the change in magnification). Specifically, a situation in which the change in magnification is large refers to a situation in which the imaging magnification has increased (i.e., the image has been magnified), and a situation in which the change in magnification is small refers to a situation in which the imaging magnification has decreased (i.e., image has been demagnified). Note that it suffices that the change in magnification increase when the image has been magnified, and decrease when image has been demagnified. The change in magnification may be the difference in imaging magnification (i.e., a positive value when the image has been magnified, and a negative value when image has been demagnified), or may be another value.

The above configuration makes it possible to change the frequency characteristics of the filter corresponding to a change in frequency component of the image due to the change in magnification. When the change in magnification is large (i.e., when the image has been magnified), the edge component is rounded, and the high-frequency component that should pass through the filter is shifted to the low-frequency side. Since it is necessary to also use the signal component shifted to the low-frequency side when calculating the AF evaluation value, the cut-off frequency of the high-pass filter is decreased. In contrast, when the change in magnification is small (i.e., when image has been demagnified), the low-frequency component that is not originally used to calculate the AF evaluation value is shifted to the high-frequency side. Since it is necessary to cut such a signal component using the filter, the cut-off frequency of the high-pass filter is increased.

The filtering section may perform the filtering process using a band-pass filter having a relatively low frequency passband when the change in magnification is relatively large. The filtering section may perform the filtering process using a band-pass filter having a relatively high frequency passband when the change in magnification is relatively small.

The above configuration makes it possible to use a band-pass filter to calculate the AF evaluation value. Note that the frequency characteristics of the filter are changed corresponding to a change in frequency component of the image due to the change in magnification in the same manner as described above in connection with the high-pass filter. Therefore, detailed description thereof is omitted.

The change-in-magnification detection section 320 may detect the ratio of a magnification evaluation value at a second timing to a magnification evaluation value at a first timing as the change in magnification at the second timing. In the first embodiment, the magnification evaluation value may be the imaging magnification. The second timing differs in time from the first timing. The magnification evaluation value is at least one of the imaging magnification and the size of the object within the image (see above).

The above configuration makes it possible to detect the ratio of the magnification evaluation values (imaging magnifications) at two different timings as the change in magnification. In this case, the change in magnification is 1 when the magnification evaluation value has not changed. The image has been magnified when the change in magnification is larger than 1, and image has been demagnified when the change in magnification is smaller than 1.

The first timing may be a timing at which the AF evaluation value starts to be calculated.

The second timing occurs after the first timing, and corresponds to the AF evaluation value calculation timing. In the first embodiment, the second timing is the current processing timing.

The above configuration makes it possible to calculate a change in the magnification evaluation value (the ratio of the magnification evaluation values in a narrow sense) relative to the timing at which the AF evaluation value starts to be calculated. The timing at which the AF evaluation value starts to be calculated may be a timing at which the AF operation starts to be performed. It is necessary to perform a process that compensates for the effects of the change in magnification in order to stably calculate the AF evaluation value (see above). In this case, it is necessary to provide a reference for the degree of compensation (i.e., the degree of change in frequency characteristics of the filter). Specifically, when the timing at which the AF evaluation value starts to be calculated is used as the first timing, the calculation process at the subsequent AF evaluation value calculation timing is performed in a state in which the change in magnification from the first timing is compensated. Therefore, the AF evaluation value can be calculated under conditions equivalent to those at the first timing. In this case, the calculated change in magnification corresponds to the cumulative magnification At (see the expression (1)).

The change in magnification is not limited to the cumulative magnification. The first timing and the second timing may be adjacent AF evaluation value acquisition timings (see above).

The above configuration makes it possible to calculate a change in the magnification evaluation value (the ratio of the magnification evaluation values in a narrow sense) between adjacent timings. In this case, it is possible to perform a process that compensates for the change in magnification between adjacent timings. Moreover, since the change in magnification between arbitrary timings can be obtained by calculating a product of the change in magnification between adjacent timings, it is also possible to perform a process that compensates for the change in magnification between the arbitrary timings. For example, a direct product of the change in magnification from the start of the AF operation is the above cumulative magnification.

The first embodiment may be applied to an endo scope system that includes the focus control section 330 that drives (controls) the imaging optical system, the image acquisition section 310 that acquires a plurality of images captured through the imaging optical system at a different imaging magnification, and the change-in-magnification detection section 320 that detects a change in magnification. The focus control section 330 calculates the AF evaluation value that indicates the focus state of the imaging optical system based on the image acquired by the image acquisition section 310 and the change in magnification detected by the image and change-in-magnification detection section 320, and drives the imaging optical system based on the AF evaluation value to control the focus of the imaging optical system.

The endoscope system may include the light source section 100, the insertion section 200, the display section 400, the external I/F section 500, and the like (see FIG. 1).

The above configuration makes it possible to implement an endoscope system that can appropriately calculate the AF evaluation value even when using the single-lens drive configuration. Since the insertion section 200 of the endoscope system is inserted into a living body, it is desirable to reduce the size of the insertion section 200, and simplify the configuration of the imaging optical system included in the insertion section 200. Therefore, the single-lens drive configuration illustrated in FIG. 19A may be employed for the insertion section 200. In this case, it is necessary to compensate for the effects of a change in magnification as described above.

3. Second Embodiment

Figure 5:
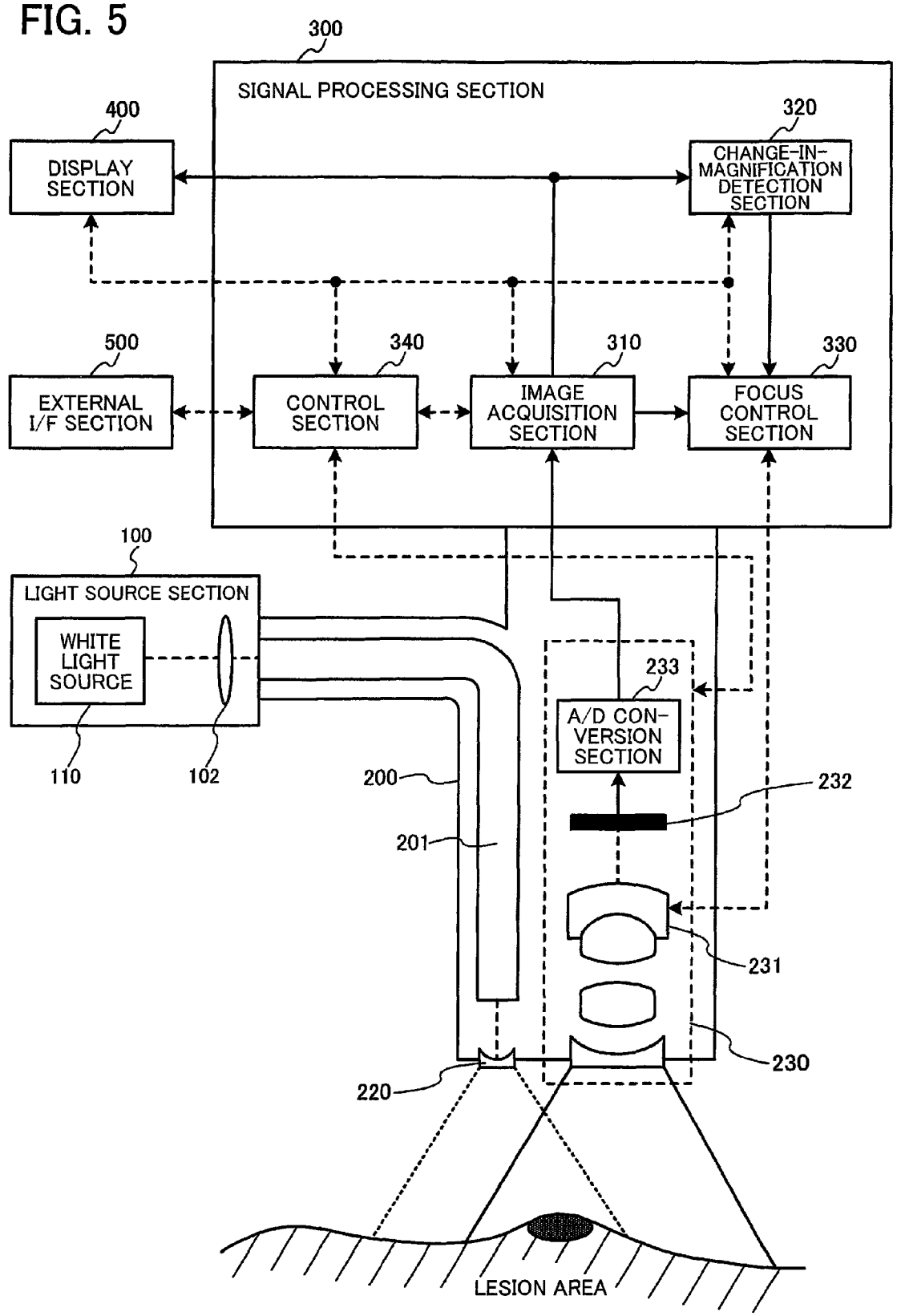
FIG. 5 illustrates a configuration example of a focus control device according to a second embodiment and an endoscope system including the same.

An endoscope system that includes a focus control device according to the second embodiment is described below with reference to FIG. 5. The endoscope system includes a light source section 100, an insertion section 200, a signal processing section 300, a display section 400, and an external I/F section 500. The elements other than the signal processing section 300 and the display section 400 are the same as those described above in connection with the first embodiment, and description thereof is omitted.

The signal processing section 300 includes an image acquisition section 310, a change-in-magnification detection section 320, a focus control section 330, and the control section 340. The image acquisition section 310 is connected to the change-in-magnification detection section 320, the focus control section 330, and the display section 400. The change-in-magnification detection section 320 is connected to the focus control section 330. The focus control section 330 is connected to the objective lens 231, and controls the magnification and the in-focus object plane position by controlling the objective lens 231 using a lens control signal. The control section 340 is bidirectionally connected to the imaging section 230, the change-in-magnification detection section 320, the focus control section 330, the image acquisition section 310, the display section 400, and the external I/F section 500, and controls the imaging section 230, the change-in-magnification detection section 320, the focus control section 330, the image acquisition section 310, the display section 400, and the external I/F section 500.

The image acquisition section 310 is configured in the same manner as described above in connection with the first embodiment, and description thereof is omitted. An endoscopic image acquired by the image acquisition section 310 is output to the change-in-magnification detection section 320.

Figure 6:
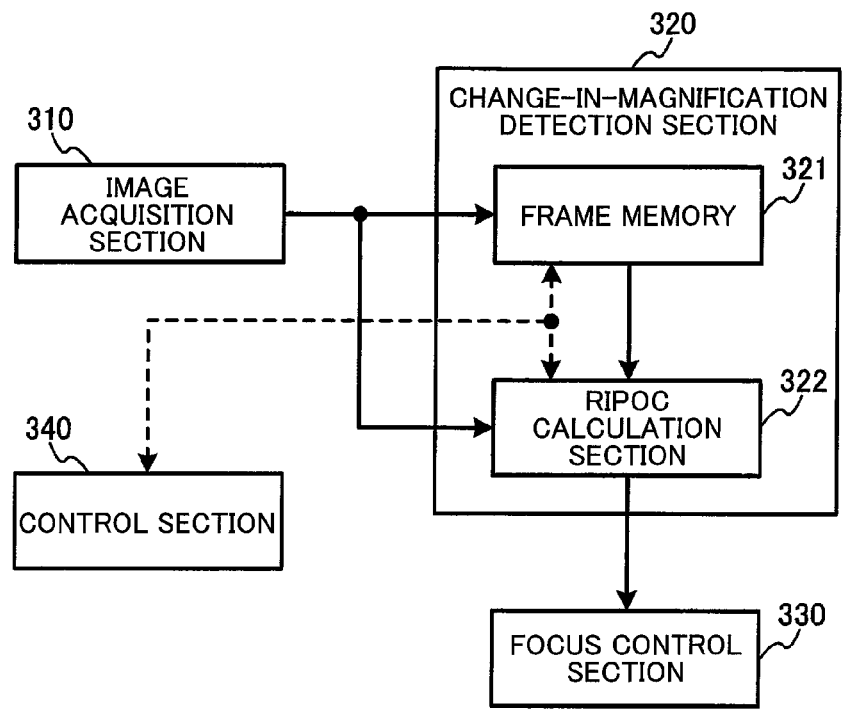
FIG. 6 illustrates a configuration example of a change-in-magnification detection section according to the second embodiment.

The change-in-magnification detection section 320 detects a change in size of the object within the endoscopic image as the change in magnification based on the pixel values of the endoscopic image output from the image acquisition section 310. The detected change in magnification is output to the focus control section 330. The configuration of the change-in-magnification detection section 320 according to the second embodiment is described below with reference to FIG. 6. The change-in-magnification detection section 320 includes a frame memory 321 and an RIPOC calculation section 322. The endoscopic image output from the image acquisition section 310 is output to the frame memory 321 and the RIPOC calculation section 322. The frame memory 321 is connected to the RIPOC calculation section 322. The RIPOC calculation section 322 is connected to the focus control section 330.

The frame memory 321 outputs the endoscopic image output from the image acquisition section 310 to the RIPOC calculation section 322 with a delay of one frame.

The RIPOC calculation section 322 detects a change in size of the object within each endoscopic image as the change in magnification based on the endoscopic image output from the image acquisition section 310 and the endoscopic image output from the frame memory 321. The endoscopic image output from the image acquisition section 310 is hereinafter referred to as "current image", and the endoscopic image output from the frame memory 321 is hereinafter referred to as "preceding image" for convenience of explanation. Note that a technique that calculates the change in magnification from the current image and the preceding image (i.e., rotation-invariant phase-only correlation technique (RIPOC technique) is known in the art, and detailed description thereof is omitted. The RIPOC technique is described in detail in "Rotation Measurements using Rotation Invariant Phase-only correlation", The journal of the Institute of Image Information and Television Engineers, 22 (45), 55-60, 1998-09-14. The RIPOC technique can detect the translation, the change in size, and the rotation of the object within the current image relative to the preceding image. The change in size of the object is output to the focus control section 330 as the change in magnification.

Figure 7:
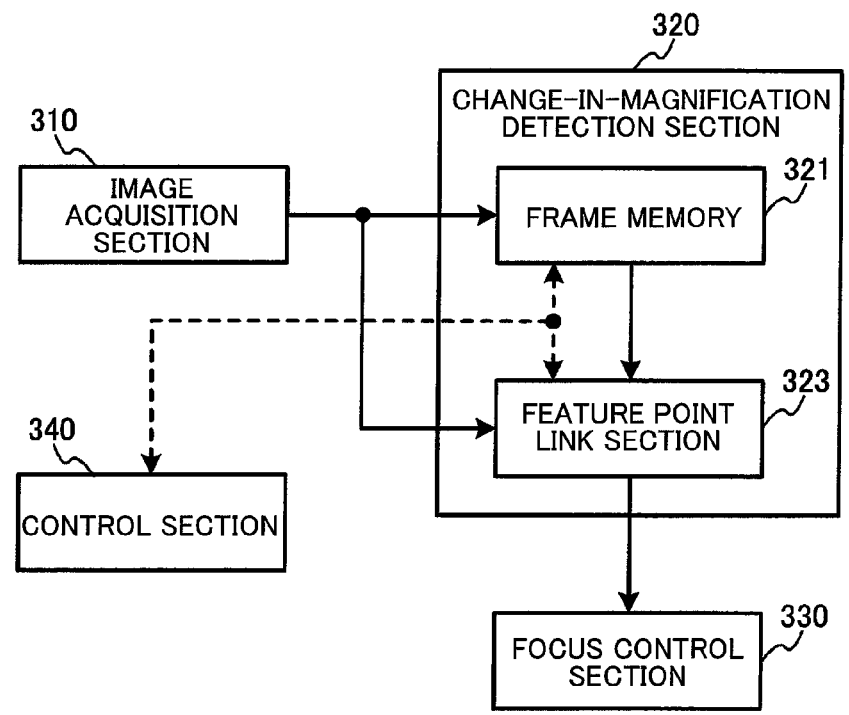
FIG. 7 illustrates another configuration example of a change-in-magnification detection section according to the second embodiment.

A modification of the change-in-magnification detection section 320 according to the second embodiment is described below with reference to FIG. 7. The change-in-magnification detection section 320 includes a frame memory 321 and a feature point link section 323. The endoscopic image output from the image acquisition section 310 is output to the frame memory 321 and the feature point link section 323. The frame memory 321 is connected to the feature point link section 323. The feature point link section 323 is connected to the focus control section 330.

The frame memory 321 outputs the endoscopic image output from the image acquisition section 310 to the feature point link section 323 with a delay of one frame.

The feature point link section 323 detects feature points from the current image output from the image acquisition section 310 and the preceding image output from the frame memory 321, and detects the change in magnification of the current image and the preceding image from the relationship between the feature points. Note that a technique that detects the feature points from the current image and the preceding image is known in the art, and detailed description thereof is omitted. The feature points are detected based on a known SIFT feature quantity. The SIFT feature quantity is a feature quantity that is robust to the rotation, the change in scale, and the change in illumination of the image. The SIFT feature quantity is described in detail in David G Lowe, "Distinctive image features from scale-invariant keypoints", Journal of Computer Vision, 60, 2, pp. 91-110, 2004. The feature points detected from the current image and the preceding image are linked between the images. The feature points are linked using a known technique, and description thereof is omitted. The relationship between the feature points is detected using the RANSAC technique. The RANSAC technique randomly extracts and combines a plurality of feature points to calculate relationship candidates, and evaluates the validity of the relationship candidates adaptively to the feature points that have not been extracted. The above calculation is repeated to determine the relationship that meets the majority of the feature points. The RANSAC technique is described in detail in M. A. Fischler and R. C. Bolles, "Random sample consensus: A paradigm for model fitting with applications to image analysis and automated cartography", Commun. ACM, No. 24, Vol. 6, pp. 381-395, June 1981. The relationship is an affine transformation (i.e., coordinate transformation). Note the coordinate transformation is a transformation from the preceding image to the current image. The affine transformation is known in the art, and detail description thereof is omitted. The affine transformation includes a translation term, a rotation term, and a scaling term, and the scaling term is output to the focus control section 330 as the change in magnification.

When the focus control section 330 has detected the start of the AF operation based on the control signal, the focus control section 330 controls the in-focus object plane position by controlling the objective lens 231 based on the endoscopic image output from the image acquisition section 310 and the change in magnification output from the change-in-magnification detection section 320. A specific configuration of the focus control section 330 according to the second embodiment is described below with reference to FIG. 8. The focus control section 330 includes a contrast value calculation section 332, a lens control section 333, and an evaluation area setting section 334. The endoscopic image output from the image acquisition section 310 is output to the contrast value calculation section 332. The change in magnification output from the change-in-magnification detection section 320 is output to the evaluation area setting section 334. The evaluation area setting section 334 is connected to the contrast value calculation section 332. The contrast value calculation section 332 is connected to the lens control section 333. The lens control section 333 is connected to the objective lens 231, and controls the objective lens 231.

Figure 9A:
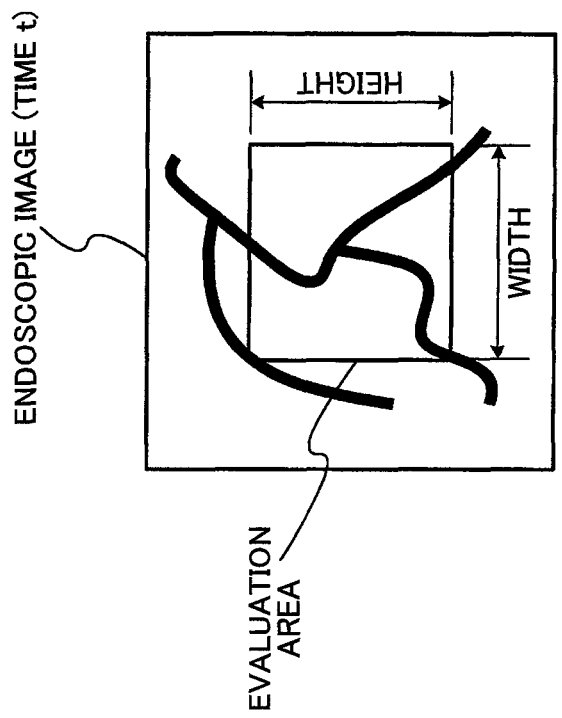
FIGS. 9A and 9B are views illustrating a method that sets an evaluation area corresponding to a change in magnification.
Figure 9B:

The evaluation area setting section 334 sets an evaluation area within the endoscopic image based on the change in magnification output from the change-in-magnification detection section 320. Specifically, when the evaluation area setting section 334 has detected the start of the AF operation based on the control signal, the evaluation area setting section 334 sets an initial evaluation area. The initial evaluation area is a rectangular area situated at the center of the endoscopic image. The size of the initial evaluation area is calculated by multiplying the size of the endoscopic image by a given ratio. The evaluation area setting section 334 scales the initial evaluation area by an evaluation area scale factor to calculate the evaluation area. The evaluation area scale factor is equal to the cumulative magnification calculated using the expression (1). The evaluation area that is set based on the evaluation area scale factor is described below with reference to FIG. 9. FIG. 9A illustrates the endoscopic image and the initial evaluation area at the start of the AF operation. FIG. 9B illustrates the endoscopic image and the evaluation area at a time t. The ratio of the size of the evaluation area illustrated in FIG. 9B to the size of the initial evaluation area illustrated in FIG. 9A is the evaluation area scale factor Vt (that is equal to the cumulative magnification At (see the expression (1))). Specifically, the size of the evaluation area increases as the evaluation area scale factor increases. The calculated evaluation area scale factor is output to the contrast value calculation section 332.

The contrast value calculation section 332 calculates the contrast value based on the evaluation area scale factor output from the evaluation area setting section 334 using the pixel values of the evaluation area set within the endoscopic image output from image acquisition section 310. Specifically, the contrast value calculation section 332 calculates the sum of the pixel values of the endoscopic image subjected to the filtering process using a high-pass filter within the evaluation area to calculate the contrast value. The calculated contrast value is output to the lens control section 333. The difference between the maximum pixel value and the minimum pixel value within the evaluation area may be used as the contrast value.

The configuration of the lens control section 333 is the same as described above in connection with the first embodiment, and description thereof is omitted.

It is possible to reduce the effects of the change in magnification on the contrast value, and stably implement the AF operation by thus setting the evaluation area for calculating the contrast value so that the change in magnification is compensated.

Figure 10:
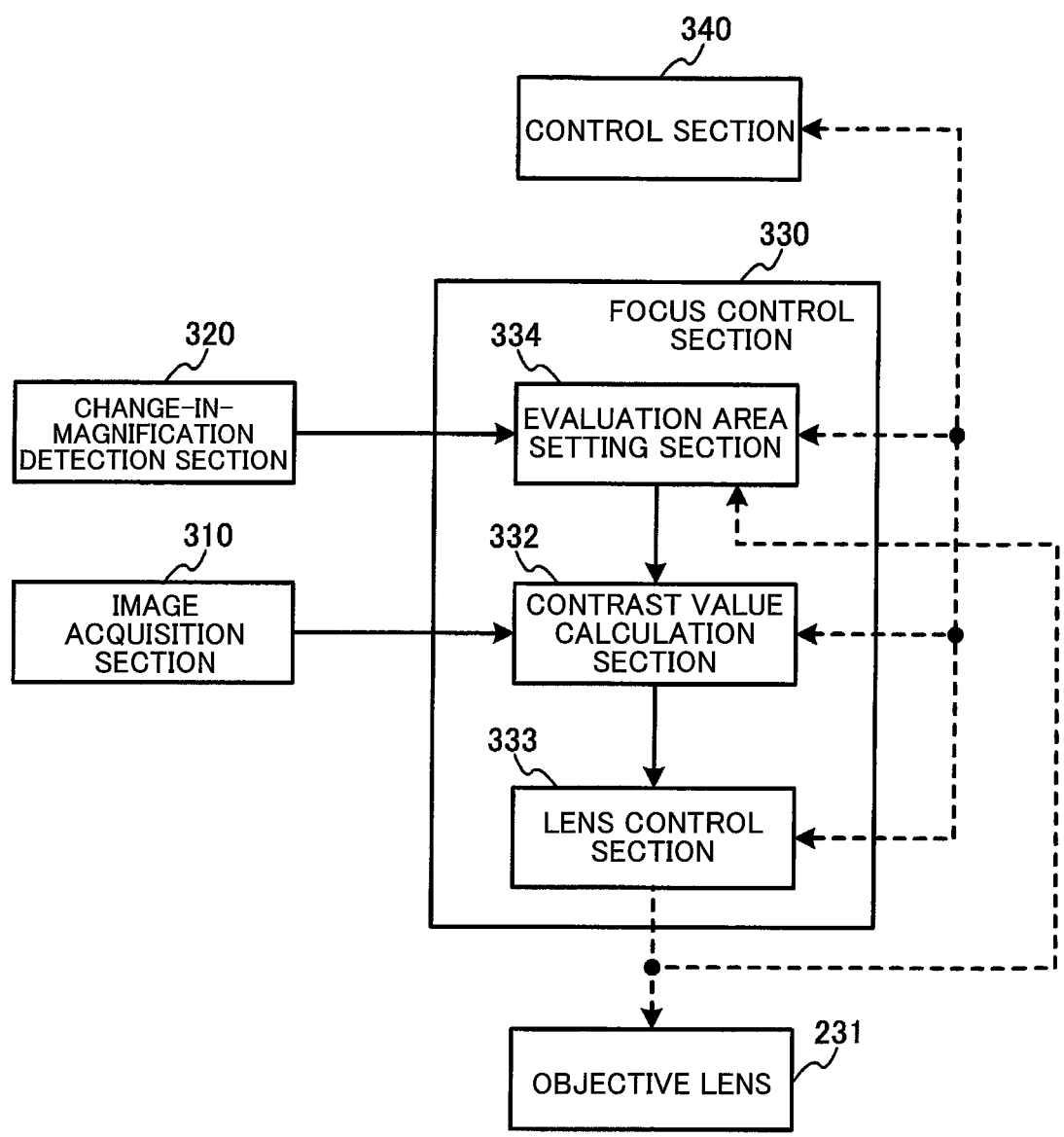
FIG. 10 illustrates another configuration example of a focus control section according to the second embodiment.
Figure 11A:
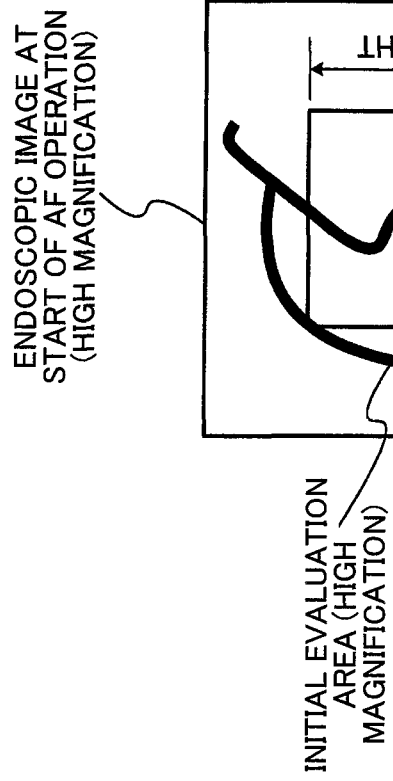
FIGS. 11A and 11B are views illustrating an initial evaluation area setting method.
Figure 11B:
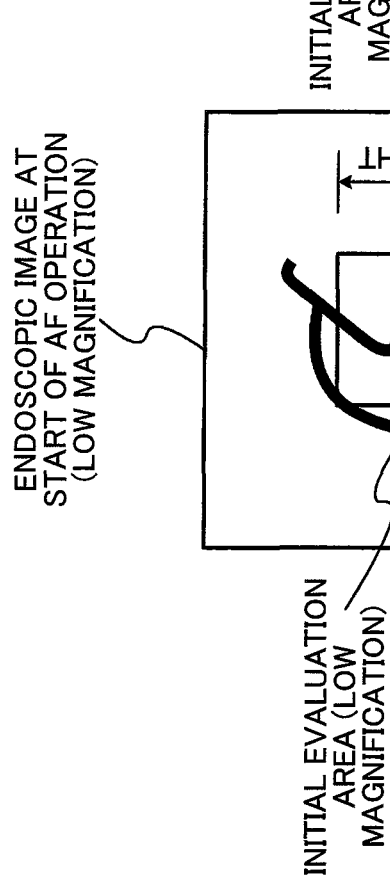

The size of the initial evaluation area is calculated by multiplying the size of the endoscopic image by a given ratio as described above. The given ratio may be variable corresponding to the magnification of the objective lens 231 at the start of the AF operation. The given ratio is referred to as "initial evaluation area scale factor" for convenience of explanation. FIG. 10 illustrates the configuration of the focus control section 330 employed in such a case. The configuration of the focus control section 330 illustrated in FIG. 10 differs from the configuration of the focus control section 330 described above with reference to FIG. 9 in that the lens control signal is also output to the evaluation area setting section 334. The evaluation area setting section 334 acquires the magnification of the objective lens 231 at the start of the AF operation based on the lens control signal. The relationship between the initial evaluation magnification and the magnification at the start of the AF operation is described below with reference to FIG. 11. In FIG. 11B, the initial evaluation magnification is increased since the magnification is high as compared with FIG. 11A. The frequency that the evaluation area scale factor exceeds 1.0 (or becomes close to 0.0) due to the change in magnification can be reduced by thus setting the initial evaluation magnification. Specifically, it is likely that the object is observed at a higher magnification when the magnification at the start of the AF operation is low, and observed at a lower magnification when the magnification at the start of the AF operation is high. It is necessary to avoid the above situation for the reasons described below. If the evaluation area scale factor exceeds 1.0, it may be necessary to calculate the contrast value in an area larger than the endoscopic image. However, since the image signals are included within only the endoscopic image, the effect of the change in magnification may not be sufficiently reduced from the contrast value. If the evaluation area scale factor is close to 0.0, the contrast value is calculated from a very small evaluation area, and the AF operation becomes unstable.

The display section 400 displays (outputs) the endoscopic image output from the image acquisition section 310 on an image display device (e.g., endoscope monitor).

According to one aspect of the invention, the endoscopic image is acquired through the endoscopic imaging optical system that is configured so that the magnification and the in-focus object plane position are changed in synchronization. A change in magnification of the endoscopic imaging optical system is detected from the endoscopic image. The evaluation area is set within the endoscopic image so that the size of the evaluation area is variable to compensate for the detected change in magnification, and the filtering process using a high-pass filter is performed on the pixels within the evaluation area to calculate the contrast value. The AF operation (function) is implemented by controlling the imaging optical system so that the calculated contrast value becomes a maximum. The AF operation can be stably performed corresponding to the change in magnification by calculating the contrast value from the evaluation area of which the size has been changed to compensate for the change in magnification.

Figure 8:
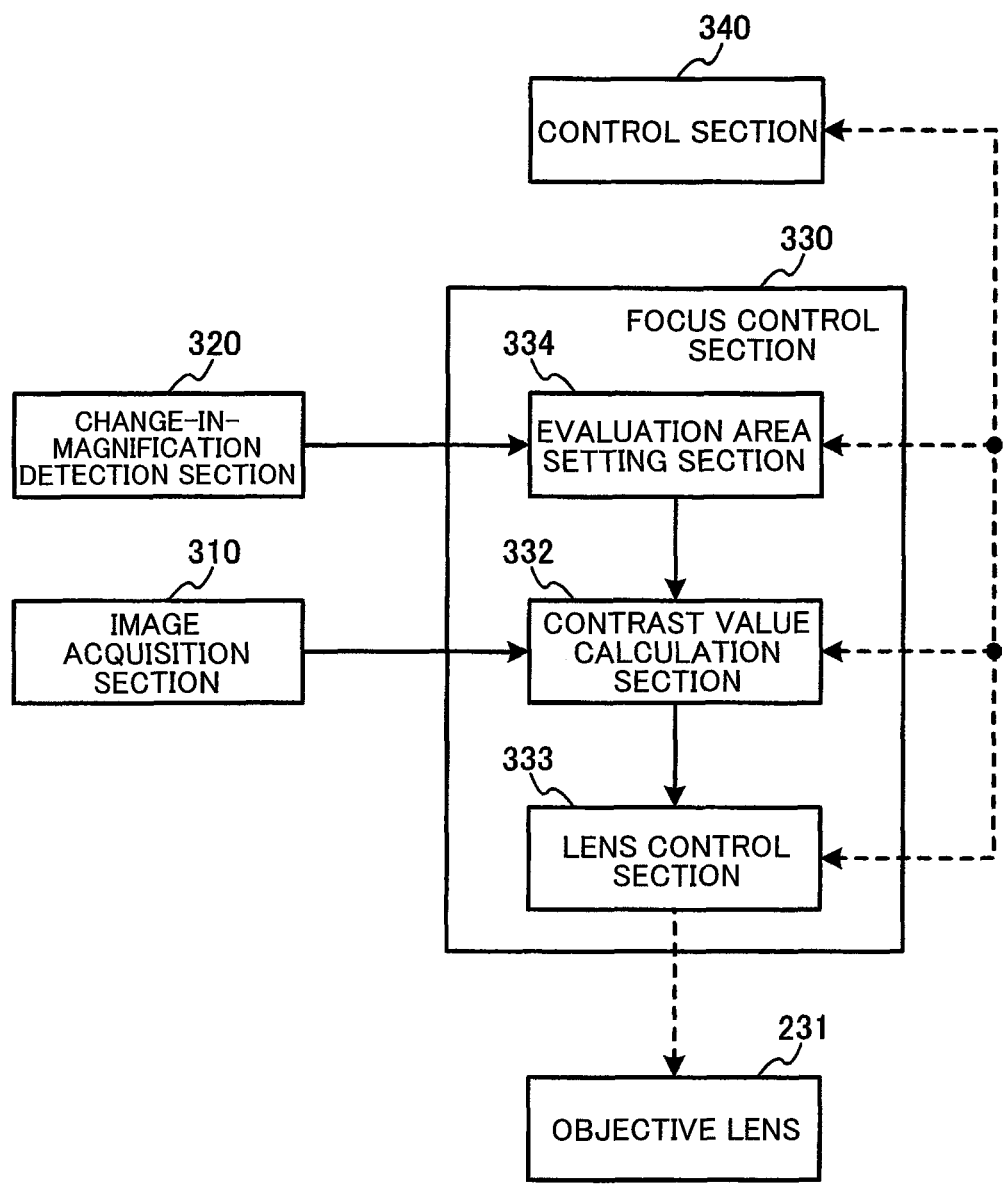
FIG. 8 illustrates a configuration example of a focus control section according to the second embodiment.

According to the second embodiment, the focus control section 330 includes the evaluation area setting section 334 that sets the evaluation area within the image, the evaluation area being an area that includes pixels used to calculate the AF evaluation value (see FIG. 8). The evaluation area setting section 334 changes the size of the evaluation area based on the change in magnification.

The evaluation area is an area that includes pixels used to calculate the AF evaluation value, and the object corresponding to the pixels used to calculate the AF evaluation value is brought into focus. Therefore, it is desirable that the evaluation area be set to the focus target area (position) within the image. However, since it is difficult to automatically determine the focus target area within the image, and it is considered that the user pays attention to the center of the image during zoom observation, the evaluation area is set at the center of the image. Although FIG. 9A and the like illustrate a rectangular area as the evaluation area, the shape of the evaluation area is not limited thereto.

According to the above configuration, since the evaluation area having an appropriate size can be set corresponding to the change in magnification, it is possible to stably calculate the AF evaluation value. When a change in magnification is present (e.g., when a change in magnification is not 1 (ratio)), an area that is captured through the imaging optical system and displayed within the image changes. Specifically, the size of the captured object changes. Therefore, the range of the object included within the evaluation area changes (e.g., only a narrow range of the object is included within the evaluation area after magnification). In this case, the amount of edges included in the image also changes, for example. Therefore, the size of the evaluation area is changed to compensate for the change in magnification.

The evaluation area setting section 334 may increase the size of the evaluation area when the change in magnification is relatively large. The evaluation area setting section 334 may decrease the size of the evaluation area when the change in magnification is relatively small.

The above configuration makes it possible to set the size of the evaluation area corresponding to the change in magnification. As described above, when the size of the object within the image changes, the amount of edges included within the evaluation area also changes, for example. Therefore, the size of the evaluation area may be changed so that the range of the object included within the evaluation area does not change. Specifically, the size of the evaluation area is increased when the change in magnification is large (i.e., when the image is magnified), and decreased when the change in magnification is small (i.e., when the image is demagnified).

The change-in-magnification detection section 320 may detect the change in magnification between a first timing and a second timing, and the evaluation area setting section 334 may set the evaluation area at the second timing by performing the scaling process using the change in magnification on a reference evaluation area that is the evaluation area at the first timing The first timing may be the AF operation start timing. In this case, the reference evaluation area corresponds to the initial evaluation area (see above).

The above configuration makes it possible to set the size of the evaluation area corresponding to the change in magnification. Specifically, the size of the evaluation area may be set so that the range of the object included within the evaluation area does not change. When the change in magnification indicates the ratio (Vt in FIG. 9B) of the size of the object within the image (i.e., when the size of the object is increased by a factor of Vt), the size of the evaluation area may be increased by a factor of Vt. When the evaluation area is a rectangular area (see FIGS. 9A and 9B), the size of the evaluation area is calculated by increasing the vertical dimension and the horizontal dimension by a factor of Vt. When the size of the object at the first timing is $c1$ (e.g., $c1$ pixels), and the size of the object at the second timing is $c2$, $Vt=c2/c1$. The value Vt may be calculated directly from the values $c1$ and $c2$. When using the method according to the second embodiment, the cumulative magnification At that is a direct product of the change in magnification Z between adjacent timings is calculated as the value Vt ($At=Vt$).

The evaluation area setting section 334 may increase the size of the reference evaluation area when the imaging magnification or the size of the object within the image at the first timing is relatively large. The evaluation area setting section 334 may decrease the size of the reference evaluation area when the imaging magnification or the size of the object within the image at the first timing is relatively small.

The above configuration makes it possible to appropriately set the size of the evaluation area (reference evaluation area (initial evaluation area in a narrow sense)) at the first timing. The above concept can be easily understood using the change in imaging magnification as the change in magnification. For example, when the imaging optical system is configured so that the imaging magnification can be changed from 1 to 100, it is likely that the imaging magnification does not increase to a large extent, or decreases at the second or subsequent timing when the imaging magnification at the first timing is close to 100. Therefore, it is considered that the change in magnification is small, and the evaluation area is set to be smaller than the reference evaluation area. In this case, it is desirable to increase the size of the reference evaluation area in order to prevent a situation in which the size of the evaluation area becomes too small, and it is difficult to calculate the AF evaluation value. In contrast, when the imaging magnification at the first timing is close to 1, it is considered that the change in magnification is large, and the evaluation area is set to be larger than the reference evaluation area. In this case, it is desirable to decrease the size of the reference evaluation area in order to prevent a situation in which the size of the evaluation area exceeds the size of the image (captured image or endoscopic image). When the change in magnification is determined based on the size of the object within the image, the change width is not clear, differing from the imaging magnification (e.g., 1 to 100). Therefore, it is necessary to set a reference for determining whether the size of the object at the first timing large or small. For example, an object having a clear absolute size (e.g., the thickness of a blood vessel in a given area) may be recognized from the image, and may be used as a reference for determining the size of the object within the image.

The change-in-magnification detection section 320 may detect the ratio of the size of the object at the second timing to the size of the object at the first timing as the change in magnification at the second timing. More specifically, the change-in-magnification detection section 320 may apply a phase-only correlation technique to the image at the first timing and the image at the second timing. The change-in-magnification detection section 320 may set a plurality of feature points to the image at the first timing and the image at the second timing, and detect the change in magnification based on the positions of the plurality of feature points.

The second timing differs in time from the first timing.

The above configuration makes it possible to detect the ratio of the size of the object between two different timings as the change in magnification. When the size of the object at the first timing is d1 (e.g., d1 pixels), and the size of the object at the second timing is d2, the change in magnification Zt at the second timing is expressed by Zt=d2/d1. The change in magnification may be determined using the RIPOC technique, or may be determined by setting a SIFT feature quantity, and evaluating the relationship between the feature points using the RANSAC technique.

The size of the object at each timing need not necessarily be an absolute value. For example, when a third timing differs from the first timing and the second timing, and the size (d1, d2, or d3) of the object at each timing is determined, the change in magnification between the first timing and the second timing is calculated to be d2/d1, and the change in magnification between the first timing and the third timing is calculated to be d3/d1, for example. In this case, however, it is necessary to always determine the size of the same area of the object. For example, when the distance between a first feature point and a second feature point set to the object at the first timing is used as information that indicates the size of the object, it is necessary to calculate a first corresponding point that corresponds to the first feature point and a second corresponding point that corresponds to the second feature point at the second timing and the third timing. However, the size determination target area of the object need not always be identical. For example, the change in magnification Z12 (=d2/d1) may be calculated between the first timing and the second timing, and the change in magnification Z23 (=d3'/d2') may be calculated between the second timing and the third timing. Specifically, the size determination target area of the object may differ between the case of calculating the change in magnification Z12 and the case of calculating the change in magnification Z23. In this case, the change in magnification between the first timing and the third timing cannot be calculated from the values d1 and d3', but can be calculated as the cumulative magnification by calculating "Z12×Z23".

4. Third Embodiment

An endoscope system that includes a focus control device according to the third embodiment is described below with reference to FIG. 12. The endoscope system includes a light source section 100, an insertion section 200, a signal processing section 300, a display section 400, and an external I/F section 500. The elements other than the signal processing section 300 are the same as those described above in connection with the first embodiment, and description thereof is omitted.

The signal processing section 300 includes an image acquisition section 310, a change-in-magnification detection section 320, a focus control section 330, a control section 340, and an image scaling section 350. The RAW image output from the imaging section 230 is output to the image acquisition section 310. The image acquisition section 310 is connected to the change-in-magnification detection section 320 and the image scaling section 350. The change-in-magnification detection section 320 is connected to the image scaling section 350. The image scaling section 350 is connected to the focus control section 330 and the display section 400. The focus control section 330 is connected to the objective lens 231, and controls the magnification and the in-focus object plane position by controlling the objective lens 231 using a lens control signal. The lens control signal is also output to the change-in-magnification detection section 320. The control section 340 is bidirectionally connected to the imaging section 230, the image acquisition section 310, the change-in-magnification detection section 320, the focus control section 330, the image scaling section 350, the display section 400, and the external I/F section 500, and controls the imaging section 230, the image acquisition section 310, the change-in-magnification detection section 320, the focus control section 330, the image scaling section 350, the display section 400, and the external I/F section 500 using a control signal.

The image acquisition section 310 is the same as that described above in connection with the first embodiment, and description thereof is omitted. The acquired endoscopic image is output to the change-in-magnification detection section 320 and the image scaling section 350.

The change-in-magnification detection section 320 detects a change in lens magnification based on the lens control signal output from the focus control section 330 (described below), and detects a change in object distance based on the change in lens magnification and the endoscopic image output from the image acquisition section 310. The change in lens magnification refers to a change in magnification of the objective lens 231. The change in object distance refers to a change in relative distance between the object and the objective lens 231. A specific configuration of the change-in-magnification detection section 320 according to the third embodiment is described below with reference to FIG. 13. The change-in-magnification detection section 320 according to the third embodiment includes a change-in-lens magnification detection section 324 and a change-in-distance detection section 325. The lens control signal output from the focus control section 330 (described below) is output to the change-in-lens magnification detection section 324. The endoscopic image output from the image acquisition section 310 is output to the change-in-distance detection section 325. The change-in-lens magnification detection section 324 is connected to the change-in-distance detection section 325 and the image scaling section 350. The change-in-distance detection section 325 is connected to the image scaling section 350.

The change-in-lens magnification detection section 324 detects the change in magnification and the change in lens magnification due to the movement of the objective lens 231 based on the lens control signal output from the focus control section 330. The operation of the change-in-lens magnification detection section 324 is the same as that of the change-in-magnification detection section 320 described above in connection with the first embodiment, and description thereof is omitted. Note that the term "change in lens magnification" is the same as the term "change in magnification" described above in connection with the first embodiment, but the term "change in lens magnification" is used hereinafter for convenience of explanation. The detected change in lens magnification is output to the change-in-distance detection section 325 and the image scaling section 350.

The change-in-distance detection section 325 detects a change in distance (i.e., a change in relative distance between the object and the endoscope) based on the endoscopic image acquired by the image acquisition section 310 and the change in lens magnification output from the change-in-lens magnification detection section 324. Specifically, the change-in-distance detection section 325 detects a change in image magnification that is a temporal change in magnification of the endoscopic image. The change-in-distance detection section 325 detects a change in image magnification in the same manner as the change-in-magnification detection section 320 described above in connection with the second embodiment. Therefore, description thereof is omitted. A temporal change in magnification of the endoscopic image includes a factor due to a change in magnification of the optical system, and a factor due to a change in relative distance between the object and the endoscope, and is expressed by a product of a change in magnification of the optical system and a change in relative distance between the object and the endoscope. Specifically, a change in image magnification is a product of a change in lens magnification and a change in distance, and a change in distance can be detected by dividing a change in image magnification by a change in lens magnification. The detected change in distance is output to the image scaling section 350.

When the image scaling section 350 has detected the start of the AF operation based on the control signal, the image scaling section 350 scales the endoscopic image output from the image acquisition section 310 based on the change in magnification output from the change-in-magnification detection section 320. The above process is hereinafter referred to as "scaling process". The scale factor (image scale factor) is calculated by the following expression (3) based on the change in magnification.

$$M_t = \prod_s^t \frac{1}{Z_i} = \frac{1}{A_t} \tag{3}$$

where, t is the current time, Mt is the scale factor at the current time, s is the start time of the AF operation, i is an index that indicates time, Z is the change in magnification, and A is the cumulative magnification (see the expression (1)). Specifically, the scale factor is a reciprocal of a direct product (cumulative magnification) of the change in magnification from the start of the AF operation to the current time.

Figure 14A:
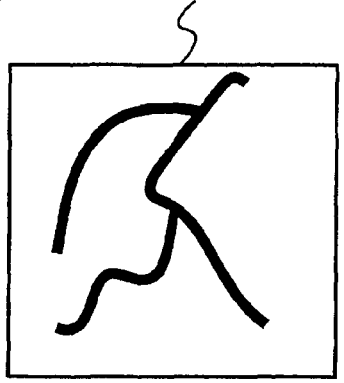
FIGS. 14A to 14C are views illustrating an example of a change in endoscopic image due to a change in magnification.

The scaling process (image scaling process) is described below with reference to FIGS. 14A to 14E. FIG. 14A illustrates the endoscopic image at the start of the AF operation. When the scale factor is larger than 1.0 (i.e., when the cumulative magnification is smaller than 1.0) (see FIG. 14B), the size of the endoscopic image is enlarged (see FIG. 14D) to obtain a scaled image. When the scale factor is smaller than 1.0 (i.e., when the cumulative magnification is larger than 1.0) (see FIG. 14C), the size of the endoscopic image is reduced (see FIG. 14E) to obtain a scaled image. The endoscopic image obtained by the scaling process is output to the focus control section 330 and the display section 400 as the scaled image. Therefore, an image that does not change in the size of the object is output to the focus control section 330 and the display section 400 during the AF operation. The focus control section 330 can calculate the contrast value (described below) while reducing the effects of a change in magnification. The display section 400 can suppress a situation in which the display magnification of the object frequently changes due to a change in magnification, and the user suffers from visually induced motion sickness. The scaling process is performed until the AF operation ends. When the AF operation is not performed, the input endoscopic image is output directly to the display section 400.

The image scaling section 350 may perform the scaling process that differs between the scaled image output to the focus control section 330 and the scaled image output to the display section 400. Specifically, the scaled image output to the display section 400 may be obtained by the scaling process using a reference scale factor calculated based on the scale factor calculated by the expression (3). The reference scale factor is calculated by the following expression (4). The scaled image output to the focus control section 330 is obtained by performing the scaling process in the same manner as described above.

$$B_t = \frac{\sum_s^t M_i}{t - s + 1} \tag{4}$$

where, Bt is the reference scale factor at the current time. Specifically, the reference scale factor is the average scale factor from the time s to the current time. The scaled image obtained by the scaling process using the reference scale factor is output to the display section 400. When the reference scale factor is not used, an image that does not change in the size of the object is displayed during the AF operation, but the user may be confused since the resolution of the image changes due to the scaling process. This is because the scaling process includes an interpolation process, and the frequency characteristics of the image change due to the interpolation process. A change in resolution can be reduced while suppressing a change in the display magnification of the object by utilizing the reference scale factor.

The scaled image output to the display section 400 may be obtained by the scaling process further based on a given allowable scale factor. In this case, the scale factor is calculated by the following expression (5).

$$M_t = \begin{cases} (1.0 + R) \times \dfrac{M_{t-1}}{Z_t} & (Z_t > 1.0 + R) \\ M_{t-1} & (1.0 - R \le Z_t \le 1.0 + R) \\ (1.0 - R) \times \dfrac{M_{t-1}}{Z_t} & (Z_t < 1.0 - R) \end{cases} \tag{5}$$

where, R is the allowable scale factor that is within the range of 0.0 to 1.0. Specifically, the scale factor is calculated while suppressing a change in the display magnification of the object within the range indicated by the allowable scale factor. Note that the range indicated by the allowable scale factor is hereinafter referred to as "allowable scaling range" for convenience of explanation. The allowable scaling range is defined for both the change-in-magnification value and the change in the display magnification of the object (e.g., the ratio of the size of the object in FIG. 15E to the size of the object in FIG. 15B). Note that the values that specify the allowable scaling range for the change-in-magnification value and the change in the display magnification of the object are equal. The scaling process that utilizes the allowable scaling range is described below with reference to FIGS. 16A to 16E. FIGS. 16A to 16E illustrate an example in which the change-in-magnification value at the time t exceeds the allowable scaling range. FIG. 16A illustrates the endoscopic image acquired at the time t−1. FIG. 16B illustrates the scaled image obtained by the scaling process at the time t−1. FIG. 16C illustrates the endoscopic image acquired at the time t. FIG. 16D illustrates the scaled image obtained by the scaling process so that the display magnification of the object is equal to that of the endoscopic image illustrated in FIG. 16B. FIG. 16E illustrates the scaled image in which the change in the display magnification of the object is allowed up to the upper limit of the allowable scaling range. FIGS. 17A to 17E illustrate an example in which the change-in-magnification value at the time t is smaller than the allowable scaling range. FIG. 17A illustrates the endoscopic image acquired at the time t−1. FIG. 17B illustrates the scaled image obtained by the scaling process at the time t−1. FIG. 17C illustrates the endoscopic image acquired at the time t. FIG. 17D illustrates the scaled image obtained by the scaling process so that the display magnification of the object is equal to that of the endoscopic image illustrated in FIG. 17B. FIG. 17E illustrates the scaled image in which the change in the display magnification of the object is allowed up to the lower limit of the allowable scaling range. The above configuration makes it possible to reduce a change in resolution while suppressing a change in display magnification within the allowable scaling range so that the user does not suffer from visually induced motion sickness.

The image scaling section 350 may perform the scaling process using the scale factor calculated based on the change-in-magnification value that differs between the scaled image output to the focus control section 330 and the scaled image output to the display section 400. Specifically, the scaled image output to the focus control section 330 may be obtained by the scaling process using a product of the change in lens magnification output from the change-in-lens magnification detection section 324 and the change in distance output from the change-in-distance detection section 325. The scaled image output to the display section 400 is obtained by performing the scaling process to compensate for only the change in lens magnification. The above configuration makes it possible to stably perform the AF operation corresponding to a change in frequency characteristics of the endoscopic image due to a change in relative distance to the object. The gap (difference) between the change in relative distance to the object and the displayed image due to the operation performed on the endoscope can be reduced by compensating for only the change in lens magnification without compensating for the change in distance.

The scaling process for obtaining the scaled image output to the display section 400 may be continued after the AF operation has ended. Specifically, the scaling process may be continued after the AF operation has ended until the scale factor Mt (see the expression (5)) satisfies the following expression (6).

$$M_t = \begin{cases} (1.0 - R) \times M_{t-1} & \left(M_{t-1} > \frac{1.0}{1.0 - R}\right) \\ 1.0 & \left(\frac{1.0}{1.0 + R} \leq M_{t-1} \leq \frac{1.0}{1.0 - R}\right) \\ (1.0 + R) \times M_{t-1} & \left(M_{t-1} < \frac{1.0}{1.0 + R}\right) \end{cases} \quad (6)$$

Note that the scale factor Mt after the AF operation has ended is calculated using only the expression (6) independently of the change-in-magnification value. Alternatively, the scaling process may be continued until a given time elapses.

If the scaling process for obtaining the scaled image output to the display section 400 is suddenly stopped after the AF operation has ended, the display magnification of the object may change to a large extent after the AF operation has ended, and the user may be confused. The above configuration makes it implement a gradual change in display magnification after the AF operation has ended, and suppress a situation in which the user is confused.

Figure 18:
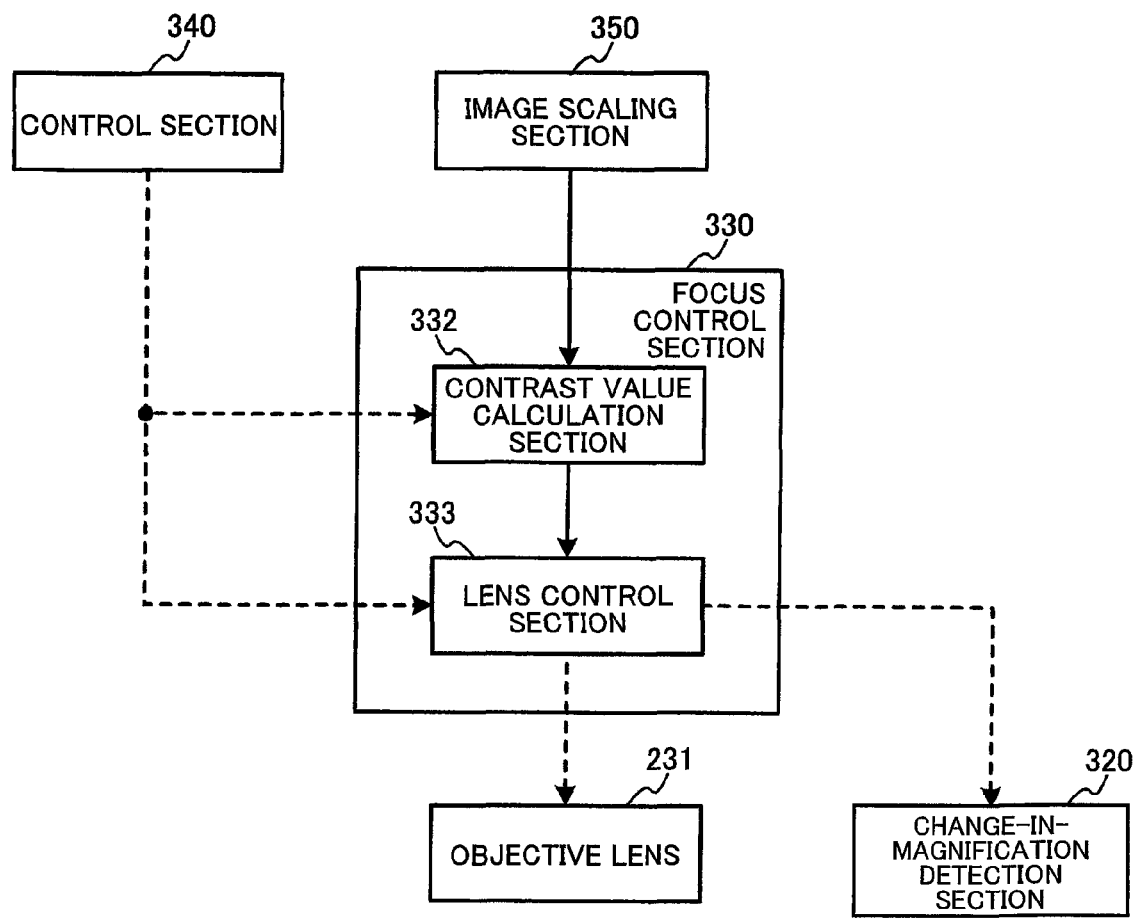
FIG. 18 illustrates a configuration example of a focus control section according to the third embodiment.

When the focus control section 330 has detected the start of the AF operation based on the control signal, the focus control section 330 controls the in-focus object plane position by controlling the objective lens 231 based on the pixel values of the scaled image output from the image scaling section 350 (described below). A specific configuration of the focus control section 330 is described below with reference to FIG. 18. The focus control section 330 includes a contrast value calculation section 332 and a lens control section 333. The scaled image output from the image scaling section 350 is output to the contrast value calculation section 332. The contrast value calculation section 332 is connected to the lens control section 333. The lens control section 333 is connected to the objective lens 231, and outputs the lens control signal to control the objective lens 231. The lens control signal is also output to the change-in-magnification detection section 320.

The contrast value calculation section 332 performs a filtering process on the scaled image output from the image scaling section 350 to calculate the contrast value. The contrast value refers to the sum of the pixel values of the scaled image subjected to the filtering process within a rectangular area that has a given size and is situated at the center of the scaled image. A filter used for the filtering process is a known high-pass filter. The calculated contrast value is output to the lens control section 333.

The lens control section 333 outputs the lens control signal that controls the objective lens 231 based on the contrast value output from the contrast value calculation section 332. A specific focus control method based on the contrast value is known as an AF technique, and detailed description thereof is omitted. The lens control signal is output to the objective lens 231 and the change-in-magnification detection section 320.

The display section 400 displays (outputs) the scaled image output from the image scaling section 350 on an image display device (e.g., endoscope monitor). When the size of the scaled image is larger than the displayable image size, an image having the displayable image size is extracted from the center of the scaled image, and displayed. When the size of the scaled image is smaller than the displayable image size, the scaled image is displayed at the center of the display, and the remaining display area is displayed in black. The output image (i.e., the endoscopic image when the AF operation is not performed, or the scaled image when the AF operation is performed) may always be scaled (enlarged in size) to some extent, and the center area thereof may be displayed. This makes it possible to suppress a situation in which the display area is frequently displayed in black.

An example in which the change-in-distance detection section 325 calculates the change in distance from the change in magnification of the optical system and the change in magnification of the image has been described above. However, when the endoscope includes a ranging means (e.g., a triangulation means having a twin-lens configuration), the change in distance may be calculated directly using the ranging means.

According to one aspect of the invention, the endoscopic image is acquired through the endoscopic imaging optical system that is configured so that the magnification and the in-focus object plane position are changed in synchronization. A change in magnification of the endoscopic imaging optical system and a change in relative distance between the object and the endoscope are detected from the control signal output from the endoscopic imaging optical system and the endoscopic image. The endoscopic image is subjected to the scaling process based on the detected change in magnification so as to compensate for the change in magnification. The filtering process is performed on the endoscopic image subjected to the scaling process using the high-pass filter to calculate the contrast value. The AF operation (function) is implemented by controlling the imaging optical system so that the calculated contrast value becomes a maximum. The AF operation can be stably performed corresponding to the change in magnification by calculating the contrast value from the endoscopic image subjected to the scaling process so as to compensate for the change in magnification. Moreover, visually induced motion sickness due to a frequent change in the display magnification of the object can be reduced by scaling the image displayed to the user corresponding to the change in magnification. The AF operation can be stabilized, and the gap between the movement of the endoscope and the display image can be reduced by calculating the AF contrast value so as to compensate for the change in magnification of the endoscope optical system and the change in relative distance to the object, and subjecting the display image to the scaling process so as to compensate for only the change in magnification of the endoscope optical system.

Figure 12:
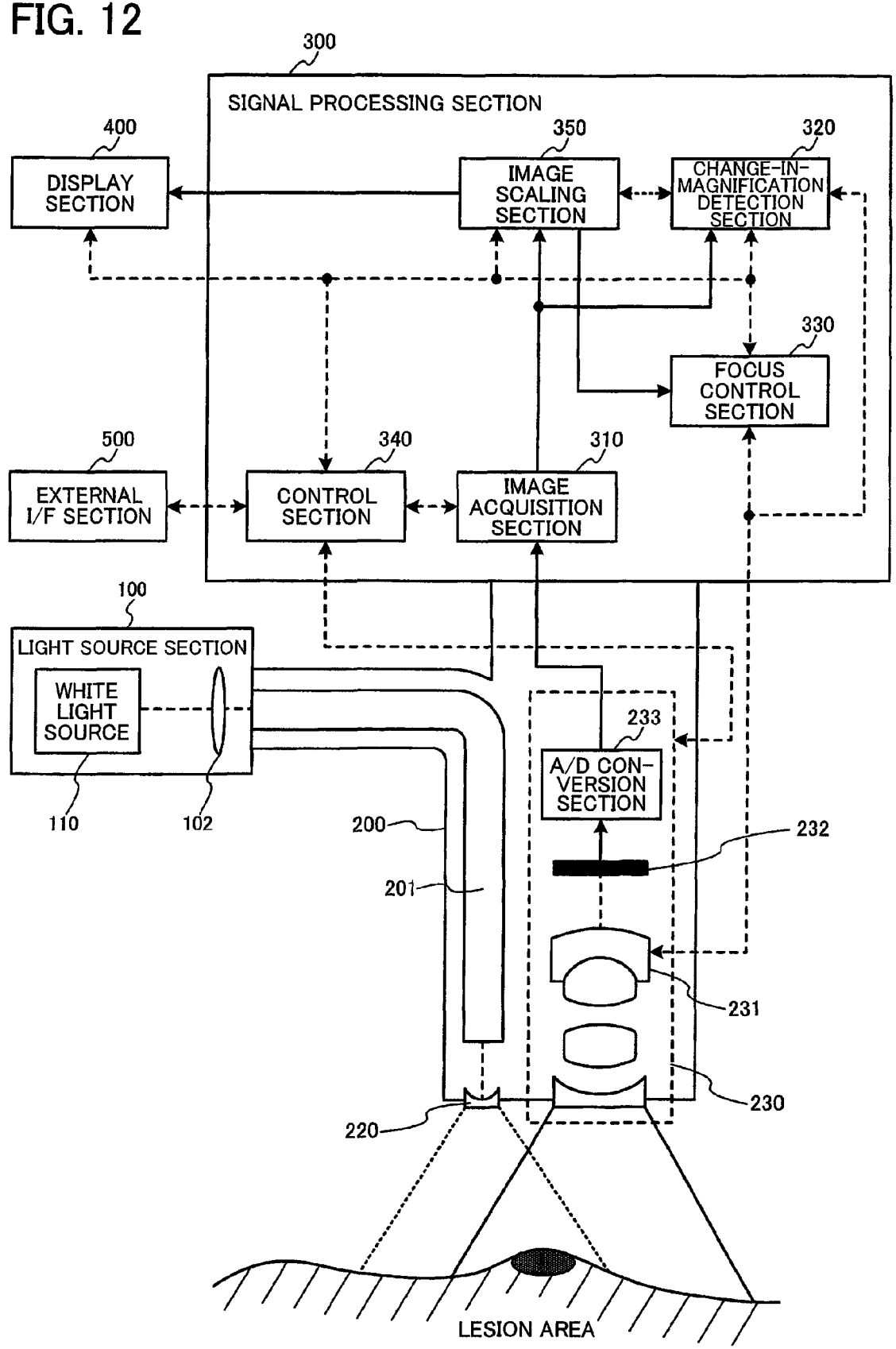
FIG. 12 illustrates a configuration example of a focus control device according to a third embodiment and an endoscope system including the same.

According to the third embodiment, the focus control device includes the image scaling section 350 that subjects the image to the image scaling process based on the change in magnification to acquire the scaled image (see FIG. 12). The focus control section 330 calculates the AF evaluation value that indicates the focus state of the imaging optical system based on the scaled image.

According to the above configuration, since a scaled image having an appropriate size can be acquired corresponding to the change in magnification, it is possible to stably calculate the AF evaluation value. In the third embodiment, the change in magnification is compensated in the same manner as in the second embodiment since the amount of edges included in the image and the like may change due to the change in magnification, and the AF evaluation value may not be appropriately calculated. The third embodiment differs from the second embodiment in that the size of the image is changed without changing the evaluation area.

The image scaling section 350 may acquire the scaled image having a relatively small size when the change in magnification is relatively large. The image scaling section 350 may acquire the scaled image having a relatively large size when the change in magnification is relatively small.

Figure 14B:
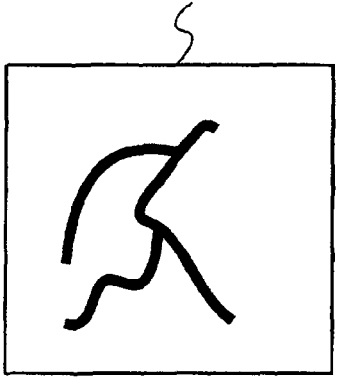
Figure 14D:
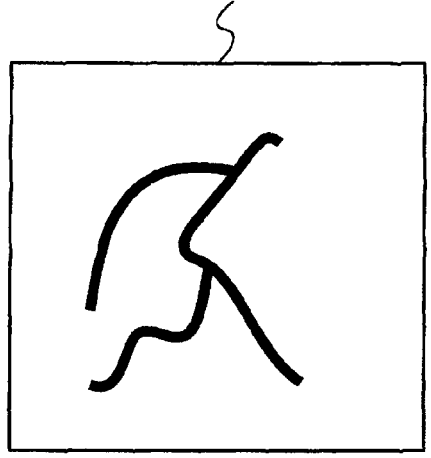
FIGS. 14D and 14E illustrate an example of a scaled image acquired corresponding to a change in magnification.
Figure 14C:
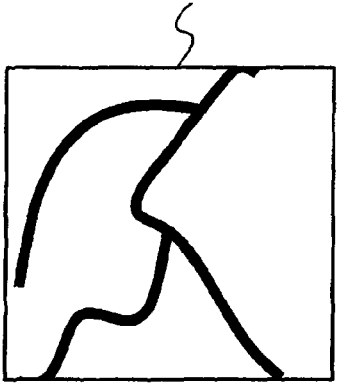
Figure 14E:
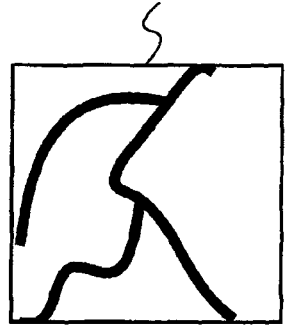

The above configuration makes it possible to acquire the scaled image having a size corresponding to the change in magnification. When the change in magnification is large (i.e., when the image (endoscopic image) has been magnified), the size reduction process is performed as the image scaling process to acquire a scaled image having a small size. This corresponds to the case where the size reduction process is performed on the image illustrated in FIG. 14C when the endoscopic image has been magnified from FIG. 14A to FIG. 14C to acquire the scaled image illustrated in FIG. 14E. Therefore, since the size of the object in FIG. 14E is equal to the size of the object in FIG. 14A, it is possible to suppress a change in the amount of edges included within the evaluation area (e.g., an area having a constant size) and the like. When the change in magnification is small (i.e., the image has been demagnified) (see FIGS. 14A and 14B), the size enlargement process may be performed on the image illustrated in FIG. 14B as the image scaling process to acquire the scaled image illustrated in FIG. 14D.

The change-in-magnification detection section 320 may detect the change in magnification between a first timing and a second timing, and the image scaling section 350 may subject the image acquired by the image acquisition section at the second timing to the image scaling process using a reciprocal of the change in magnification to acquire the scaled image.

The above configuration makes it possible to implement a process that uses a reciprocal of the change in magnification as a specific example of the image scaling process. The change in magnification refers to the ratio of the size of the object (or the imaging magnification) at the second timing to the size of the object at the first timing.

Specifically, when the size of the object at the first timing is e1 (e.g., e1 pixels), and the size of the object at the second timing is e2, the change in magnification Z is e2/e1. In this case, the scale factor (image scale factor) M used for the image scaling process is 1/Z. A specific example is described below. When the size e1 of the object at the first timing is 10 (e.g., FIG. 14A), and the size e2 of the object at the second timing is 5 (e.g., FIG. 14B), the change in magnification Z is 0.5 (=5/10). In this case, the image scaling process is performed to return the size of the object to 10. Therefore, the image scale factor M is set to 2 (=1/0.5). Since the image scaling process is performed at the second timing on the image (endoscopic image (see FIG. 14B)) acquired at the second timing, the size of the image acquired at the second timing is enlarged by a factor of 2 (scaled image (see FIG. 14D)). Therefore, the size (=5) of the object within the endoscopic image acquired at the second timing is increased to 10 by the image scaling process by a factor of 2. Accordingly, the size of the object within the scaled image obtained at the second timing can be made equal to the size (e1=10) of the object at the first timing. When the change in magnification is larger than 1 (i.e., when the image has been magnified), the size of the object is reduced in the same manner as described above.

The image scaling section 350 may output the acquired scaled image to the focus control section 330 and a display device (corresponding to the display section 400 illustrated in FIG. 12).

The above configuration makes it possible to display the scaled image acquired by the image scaling process on the display device. In the first embodiment and the second embodiment, the process that makes it possible to stably calculate the AF evaluation value is performed, but the image acquired by the image acquisition section 310 is used directly as the display image displayed on the display device (display section 400). Therefore, the display image necessarily flickers due to a change in magnification that occurs when changing the in-focus object plane position during the focus operation (e.g., wobbling during the contrast AF operation). For example, the size of the object increases and decreases when the images illustrated in FIGS. 14A to 14C are acquired in time series. In order to deal with such a situation, the scaled image acquired by the image scaling section 350 is also output to the display device. According to the above configuration, since the image subjected to the image scaling process that compensates for the change in magnification (e.g., the change in imaging magnification) is displayed, it is possible to suppress a situation in which the display image flickers. For example, the images illustrated in FIGS. 14A, 14D, and 14E are sequentially displayed as the display image when the images illustrated in FIGS. 14A to 14C are acquired in time series.

The image scaling section 350 may output a first scaled image obtained by subjecting the image to a first image scaling process to the focus control section 330, and output a second scaled image obtained by subjecting the image to a second image scaling process to the display device.

The first image scaling process and the second image scaling process are different processes. For example, the first image scaling process and the second image scaling process may differ in the image scale factor used for the image scaling process.

The above configuration makes it possible to cause the scaled image output to the focus control section 330 and the scaled image output to the display device to differ from each other. Therefore, it is possible to output an appropriate scaled image even when the scaled image appropriate for the AF evaluation value calculation process performed by the focus control section 330 differs from the scaled image that is appropriate for display on the display device.

The change-in-magnification detection section 320 may detect a first change in magnification and a second change in magnification as the change in magnification, the first change in magnification being the change in the size of the object within the image, and the second change in magnification being the change in the imaging magnification. The image scaling section 350 may output a first scaled image obtained by subjecting the image to a first image scaling process based on the first change in magnification to the focus control section 330. The image scaling section 350 may output a second scaled image obtained by subjecting the image to a second image scaling process based on the second change in magnification to the display device.

According to the above configuration, it is possible to obtain the scaled image output to the focus control section 330 by performing the image scaling process using the change in the size of the object as the change in magnification. It is also possible to obtain the scaled image output to the display device by performing the image scaling process using the change in the imaging magnification as the change in magnification. Note that the change in the imaging magnification (second change in magnification) occurs due to the change in the imaging optical system, while the change in the size of the object within the image (first change in magnification) includes a plurality of factors such as the change in the imaging magnification, and the change in relative distance between the object and the imaging section (insertion section 200). Since the image scaling process according to the third embodiment is a process that compensates for the effects of a change in magnification, it is possible to selectively compensate for a magnification change factor by appropriately selecting the change in magnification used for the first image scaling process and the second image scaling process.

The AF evaluation value calculation process performed by the focus control section 330 is implemented by image processing (e.g., extraction of the high-frequency component) on the image. Therefore, it is desirable to compensate for all of the factors (including the imaging magnification and the relative distance) that change the image during the first image scaling process that corresponds to the image output to the focus control section 330. Accordingly, the change in the size of the object within the image is used as the change in magnification (first change in magnification) used for the first image scaling process. In contrast, the image displayed on the display device may include a magnification change factor that is not desirable to compensate.

For example, when the relative distance between the imaging section and the object is compensated, the image scaling process is performed to suppress the change in the image due to the change in the relative distance. In this case, the image displayed on the display device may not be changed even when the user has moved the imaging section forward and backward. This makes it difficult to determine whether or not the operation performed by the user is reflected in the equipment, and the user may bring the imaging section too close to the object (i.e., the imaging section may collide with the object). Therefore, the change in the imaging magnification is used as the change in magnification (second change in magnification) used for the second image scaling process.

The image scaling section 350 may perform the image scaling process in a period from a first timing to an Nth timing (N is an integer equal to or larger than 2), and the change-in-magnification detection section 320 may detect an ith ($1 \le i \le N$) change in magnification at an ith timing. The image scaling section 350 may perform the second image scaling process at a kth ($1 \le k \le N$) timing based on a first change in magnification to a kth change in magnification to acquire the second scaled image, and output the second scaled image to the display device.

The above configuration makes it possible to suppress a change in resolution of the image displayed on the display device to provide a natural image. In the third embodiment, when the imaging magnification at a given reference timing is g0, and the imaging magnification at the kth timing is gk, the kth change in magnification Ak is gk/g0. Note that the change in magnification Ak corresponds to the cumulative magnification (see above), and the cumulative magnification may be calculated by a direct product of the change in magnification (i.e., the ratio of the imaging magnification) between adjacent timings. In this case, the image scaling process at the kth timing subjects the image (endoscopic image) acquired at the kth timing to the scaling process by a factor of 1/Ak to suppress the effects of the change in the imaging magnification between the reference timing and the kth timing. However, since compensation by the image scaling process necessarily scales the image, a change in resolution occurs. For example, since the size enlargement process includes a pixel value interpolation process, the edge is rounded. An image that is difficult to observe may be obtained due to a change in resolution, and may hinder observation, for example.

In order to prevent the above problem, the changes in magnification A1 to Ak−1 at the previous timings (first to k1 timings) are also used instead of using the value 1/Ak directly as the scale factor (image scale factor) used for the image scaling process. Specifically, the image scale factor Bt at a timing t may be calculated as the average image scale factor (i.e., the average value of a reciprocal of the change in magnification A) from a timing s to the timing t (see the expression (4)). According to the above configuration, the effects of the change in magnification (i.e., the effects of the change in the imaging magnification) remain to some extent, but a change in resolution can be suppressed, and it is possible to provide a natural image to the user. The image scaling section 350 may perform the image scaling process in a period from a first timing to an Nth timing (N is an integer equal to or larger than 2), and the change-in-magnification detection section 320 may detect an ith ($1 \le i \le N$) change in magnification at an ith timing. The image scaling section 350 may determine whether or not the change in magnification at an mth ($1 \le m \le N$) timing is included within a given allowable scaling range, and perform the second image scaling process at the mth timing in a way similar to the second image scaling process at an (m−1)th timing that precedes the mth timing when the change in magnification at the mth timing is included within the given allowable scaling range. The image scaling section 350 may perform the second image scaling process at the mth timing using a value closer to 1 than a reciprocal of an mth change in magnification when the change in magnification at the mth timing is not included within the given allowable scaling range.

The above configuration makes it possible to suppress a change in resolution of the image displayed on the display device to provide a natural image. Specifically, a change in resolution is suppressed in the same manner as described above by reducing the strength of the process that compensates for the effects of the change in magnification (although the effects of the change in magnification remain to some extent).

Specifically, the method represented by the expression (5) and illustrated in FIGS. 15A to 15E and the like may be employed. In the expression (5), Mt is the image scale factor at the timing t, 1.0−R to 1.0+R is the allowable scale factor (the allowable scale factor is 0.9 to 1.1 when R=0.1 (R is a positive number smaller than 1)), and Zt is the change in magnification at the timing t (e.g., the ratio of the imaging magnification at the timing t to the imaging magnification at the timing t−1). When 1.0−R≤Zt≤1.0+R (i.e., when the change in magnification (e.g., the change in the size of the object within the image (may be the change in the imaging magnification)) is within the allowable scale factor), the image scale factor Mt−1 at the timing t−1 is used as the image scale factor Mt at the timing t. Since the change in magnification is Zt, the size of the object within the image illustrated in FIG. 15C is enlarged by a factor of Zt as compared with FIG. 15A. Since the image scale factor at the timing t−1 is Mt−1, the size of the object within the image illustrated in FIG. 15B (i.e., the display image (scaled image) at the timing t−1) is enlarged by a factor of Mt−1 as compared with FIG. 15A. Since the image scaling process for stably calculating the AF evaluation value is a process that maintains the size of the object within the image to be equal, the size of the object within the scaled image at the timing t must be made equal to that of FIG. 15B. Since the ratio of the size of the object in FIG. 15C to the size of the object in FIG. 15A is Zt, and the ratio of the size of the object in FIG. 15B to the size of the object in FIG. 15A is Mt−1, the image illustrated in FIG. 15D obtained by subjecting the image illustrated in FIG. 15C to the image scaling process by a factor of Mt−1/Zt is normally output to the display device. However, since the effects of the change in magnification (i.e., the change in the size of the object) are allowed to some extent, the image illustrated in FIG. 15E obtained by subjecting the image illustrated in FIG. 15C to the image scaling process by a factor of Mt−1 (=Mt) is output to the display device. Specifically, the display image changes from the image illustrated in FIG. 15B to the image illustrated in FIG. 15E, and the size of the object differs by a factor of Zt.

When the change in magnification is outside the allowable scale factor (e.g., when Zt<1.0−R), the image is scaled as illustrated in FIGS. 16A to 16E. When the size of the object within the scaled image is not changed at the timings t−1 and t, the scaled image illustrated in FIG. 16D is obtained at the timing t. When using the scaled image illustrated in FIG. 16D, since the value Zt is outside the allowable scale factor, the size enlargement process is performed using a large image scale factor, and the resolution significantly changes from FIG. 16B to FIG. 16D. Therefore, the scaled image illustrated in FIG. 16E is calculated using Mt=(1.0−R)Mt−1/Zt. This makes it possible to adjust the ratio of the size of the object in FIG. 15E to the size of the object in FIG. 16B to 1.0−R. Specifically, when the change in magnification is smaller than the lower limit of the allowable scale factor, the image scaling process is performed so that the change in the size of the object within the display image is equal to the lower limit.

As illustrated in FIGS. 17A to 17E, when the change in magnification is larger than the upper limit of the allowable scale factor, the image scaling process is performed so that the change in the size of the object within the display image is equal to the upper limit. Specifically, the scaled image corresponding to the change in magnification is output, and the change in the size of the object is allowed when the change in the size of the object within the display image between adjacent timings is within the allowable scale factor range. According to the above configuration, the effects of the change in magnification remain to some extent, but a change in resolution can be suppressed, and it is possible to provide a natural image to the user.

Figure 13:
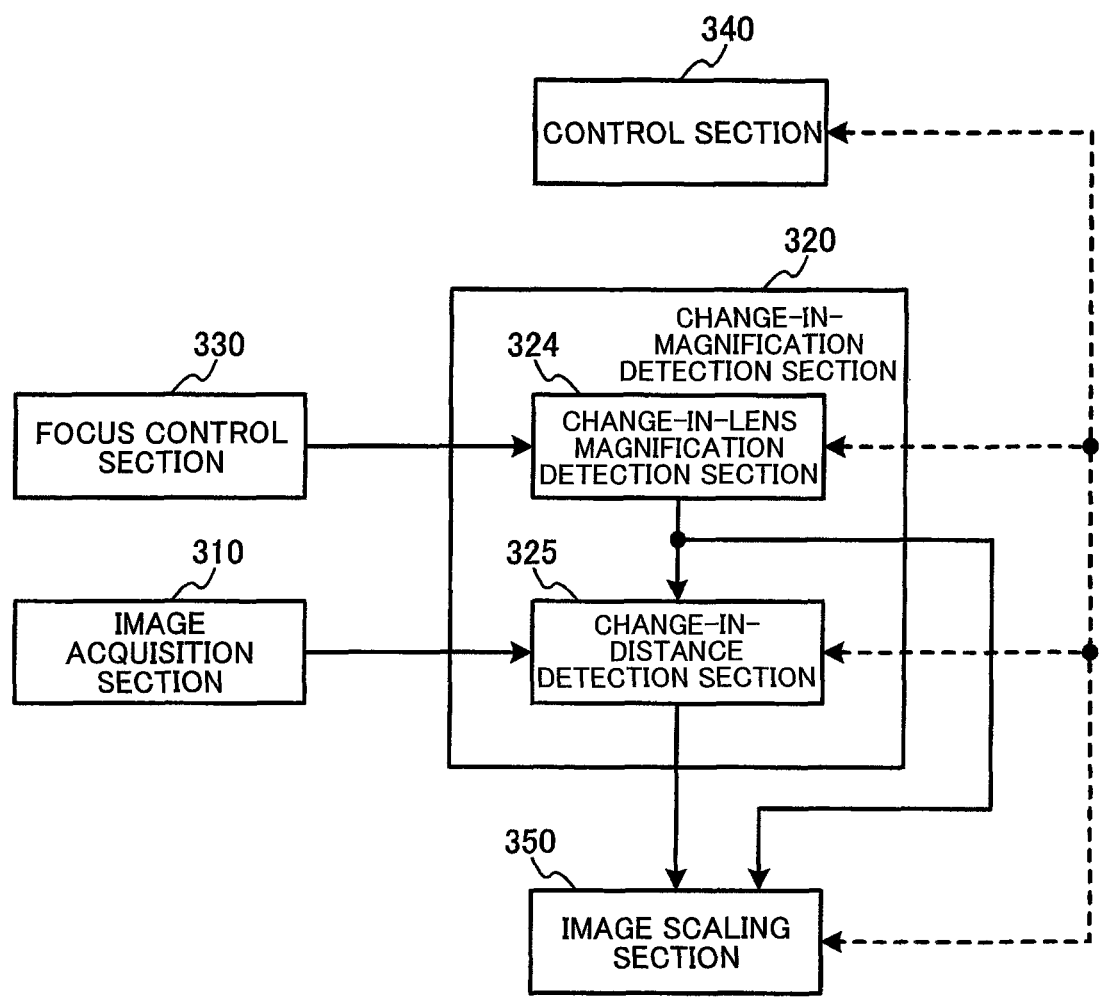
FIG. 13 illustrates a configuration example of a change-in-magnification detection section according to the third embodiment.

The change-in-magnification detection section 320 may include the change-in-distance detection section 325 that detects a change in distance information about the distance from the imaging optical system to the object (see FIG. 13). The change-in-distance detection section 325 may detect the change in the distance information based on the change in the imaging magnification and the change in the size of the object.

The above configuration makes it possible to detect the change in the distance information that indicates the relative distance from the imaging optical system to the object. The size of the object within the image may change due to the change in the imaging magnification and the change in the distance information. Therefore, when other factors can be disregarded, the change in the imaging magnification is N, and the change in the distance information is M, the first change in magnification that is the change in the imaging magnification is expressed by N, and the second change in magnification that is the change in the size of the object is expressed by N×M. Accordingly, the value M is calculated by dividing the second change in magnification by the first change in magnification. Since M is the change in the distance information (e.g., the ratio of the distance information between two timings), it may be necessary to perform an additional process when calculating the distance at each timing.

5. Fourth Embodiment

As described above in connection with the third embodiment, it is desirable to display the image obtained by the magnification change process on the display section 400 so that the user can easily perform diagnosis. However, the method according to the third embodiment does not take account of the case where the change in magnification includes a factor other than a factor due to wobbling.

Specifically, when driving the zoom lens (wobbling) in order to calculate the AF evaluation value while driving the zoom lens in order to change the imaging magnification (e.g., in order to magnify the object), a high-frequency change in magnification due to wobbling and a low-frequency change in magnification due to an intentional change in magnification are synthesized (see FIG. 23, for example), and detected by the change-in-magnification detection section 320 as the change in magnification.

Since the high-frequency change in magnification due to wobbling hinders observation or diagnosis, it is desirable to perform the image scaling process that suppresses the high-frequency change in magnification due to wobbling. On the other hand, since the low-frequency change in magnification is due to the movement of the zoom lens that reflects the user's intention, it is not desirable to suppress the low-frequency change in magnification. For example, when the user has instructed to drive the zoom lens in order to magnify the object, the image displayed on the display section 400 may not reflect the instruction issued by the user (i.e., the size of the object may not change).

In the fourth embodiment, a high-frequency change in magnification due to wobbling is detected based on the change in magnification (including the change in magnification Z[t] and the cumulative magnification A[t]) output from the change-in-magnification detection section 320, and separated from a low-frequency change in magnification to maintain the effects of the low-frequency change in magnification on the display image while suppressing the effects of the high-frequency change in magnification on the display image.

When detecting the change in magnification from the size of the object, a similar problem occurs when the imaging section 230 approaches the object (i.e., when the distance between the object and the imaging section 230 changes in the optical axis direction of the imaging section 230). Specifically, since the size of the object within the image also changes due to the change in distance, the high-frequency change in magnification due to wobbling and the low-frequency change in magnification due to the change in distance are detected by the change-in-magnification detection section 320 as the change in magnification. When detecting the change in magnification based on the control information from the imaging optical system, the detected change in magnification is not affected by the change in distance. Therefore, an unnecessary image scaling process (i.e., a process that suppress a change in angle of view) is not performed.

An endoscope system that includes a focus control device according to the fourth embodiment is described below with reference to FIG. 20. The endoscope system includes a light source section 100, an insertion section 200, a signal processing section 300, a display section 400, and an external I/F section 500. The elements other than the signal processing section 300 are the same as those described above in connection with the first embodiment, and description thereof is omitted.

The signal processing section 300 includes an image acquisition section 310, a change-in-magnification detection section 320, a focus control section 330, a control section 340, and an image scaling section 350. The RAW image output from the imaging section 230 is output to the image acquisition section 310. The image acquisition section 310 is connected to the change-in-magnification detection section 320, the image scaling section 350, and the focus control section 330. The change-in-magnification detection section 320 is connected to the image scaling section 350 and the focus control section 330. The image scaling section 350 is connected to the display section 400. The focus control section 330 is connected to the objective lens 231, and controls the magnification and the in-focus object plane position by controlling the objective lens 231 using a lens control signal. The control section 340 is bidirectionally connected to the imaging section 230, the image acquisition section 310, the change-in-magnification detection section 320, the focus control section 330, the image scaling section 350, the display section 400, and the external I/F section 500, and controls the imaging section 230, the image acquisition section 310, the change-in-magnification detection section 320, the focus control section 330, the image scaling section 350, the display section 400, and the external I/F section 500 using a control signal.

The change-in-magnification detection section 320 detects a change in size of the object within the endoscopic image as the change in magnification in the same manner as described above in connection with the second embodiment. Note that the change-in-magnification detection section 320 may detect the change in magnification of the objective lens 231 based on the lens control signal in the same manner as in the first embodiment, or may use both the change in size of the object and the change in magnification of the objective lens 231.

The image scaling section 350 according to the third embodiment (see FIG. 12) outputs the scaled image obtained by the image scaling process to the focus control section 330 and the display section 400. The image scaling section 350 according to the fourth embodiment outputs the scaled image (display image) to at least the display section 400. The process performed by the focus control section 330 according to the fourth embodiment may be implemented using the method according to the first embodiment, the method according to the second embodiment, or the method according to the third embodiment. When using the method according to the first embodiment or the method according to the second embodiment, it is unnecessary to output the scaled image to the focus control section 330. When using the method according to the third embodiment, it is necessary to output the scaled image to the focus control section 330.

Figure 21:
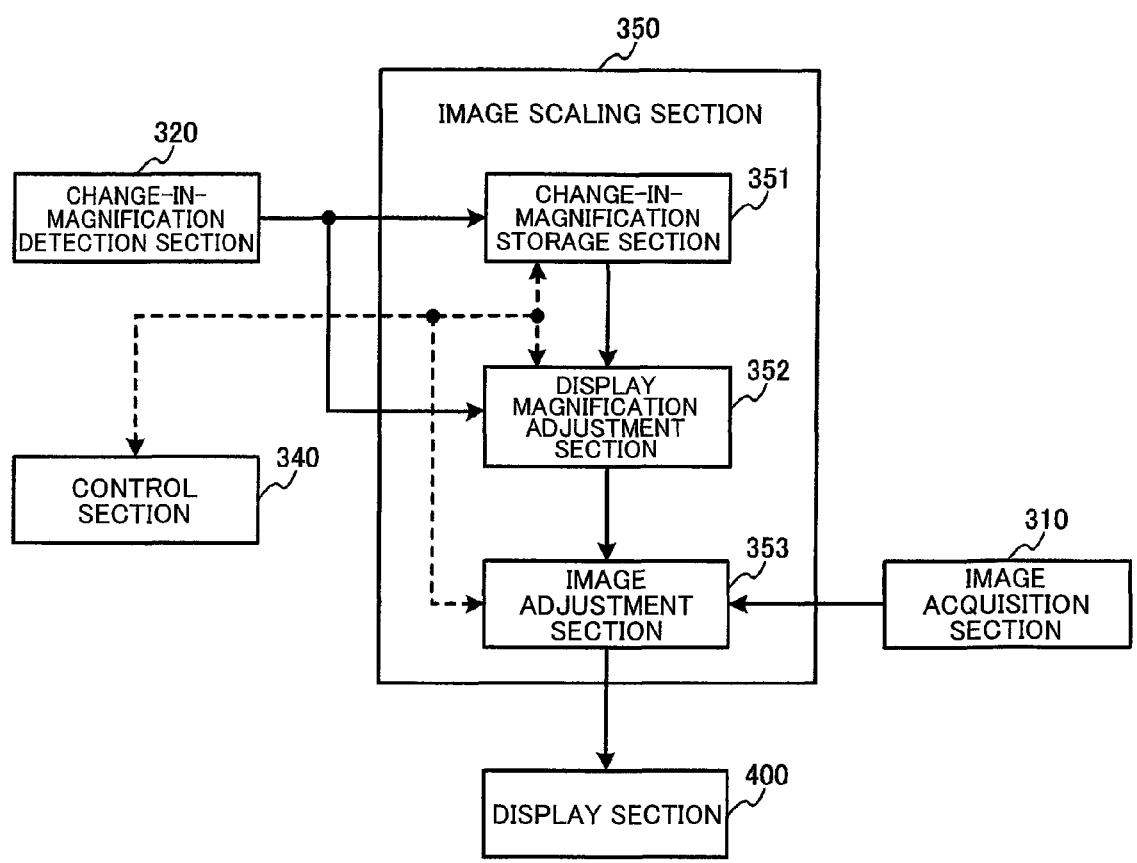
FIG. 21 illustrates a configuration example of an image scaling section according to the fourth embodiment.

The configuration of the image scaling section 350 according to the fourth embodiment is described below with reference to FIG. 21. The image scaling section 350 includes a change-in-magnification storage section 351, a display magnification adjustment section 352, and an image adjustment section 353. The change-in-magnification detection section 320 is connected to the change-in-magnification storage section 351 and the display magnification adjustment section 352. The change-in-magnification storage section 351 is connected to the display section 400 through the display magnification adjustment section 352 and the image adjustment section 353. The image acquisition section 310 is connected to the image adjustment section 353. The control section 340 is bidirectionally connected to the change-in-magnification storage section 351, the display magnification adjustment section 352, and the image adjustment section 353, and controls the change-in-magnification storage section 351, the display magnification adjustment section 352, and the image adjustment section 353 using a control signal.

The change-in-magnification detection section 320 outputs the change in magnification to the change-in-magnification storage section 351 and the display magnification adjustment section 352. The change-in-magnification detection section 320 outputs the cumulative magnification to the display magnification adjustment section 352.

The change-in-magnification storage section 351 outputs the change in magnification of the image corresponding to the current time to the display magnification adjustment section 352 with a delay of one frame.

The display magnification adjustment section 352 smoothes the high-frequency scaling component due to wobbling from the cumulative magnification based on the change in magnification and the cumulative magnification output from the change-in-magnification detection section 320, and the change in magnification in the preceding frame output from the change-in-magnification storage section 351.

Figure 22:
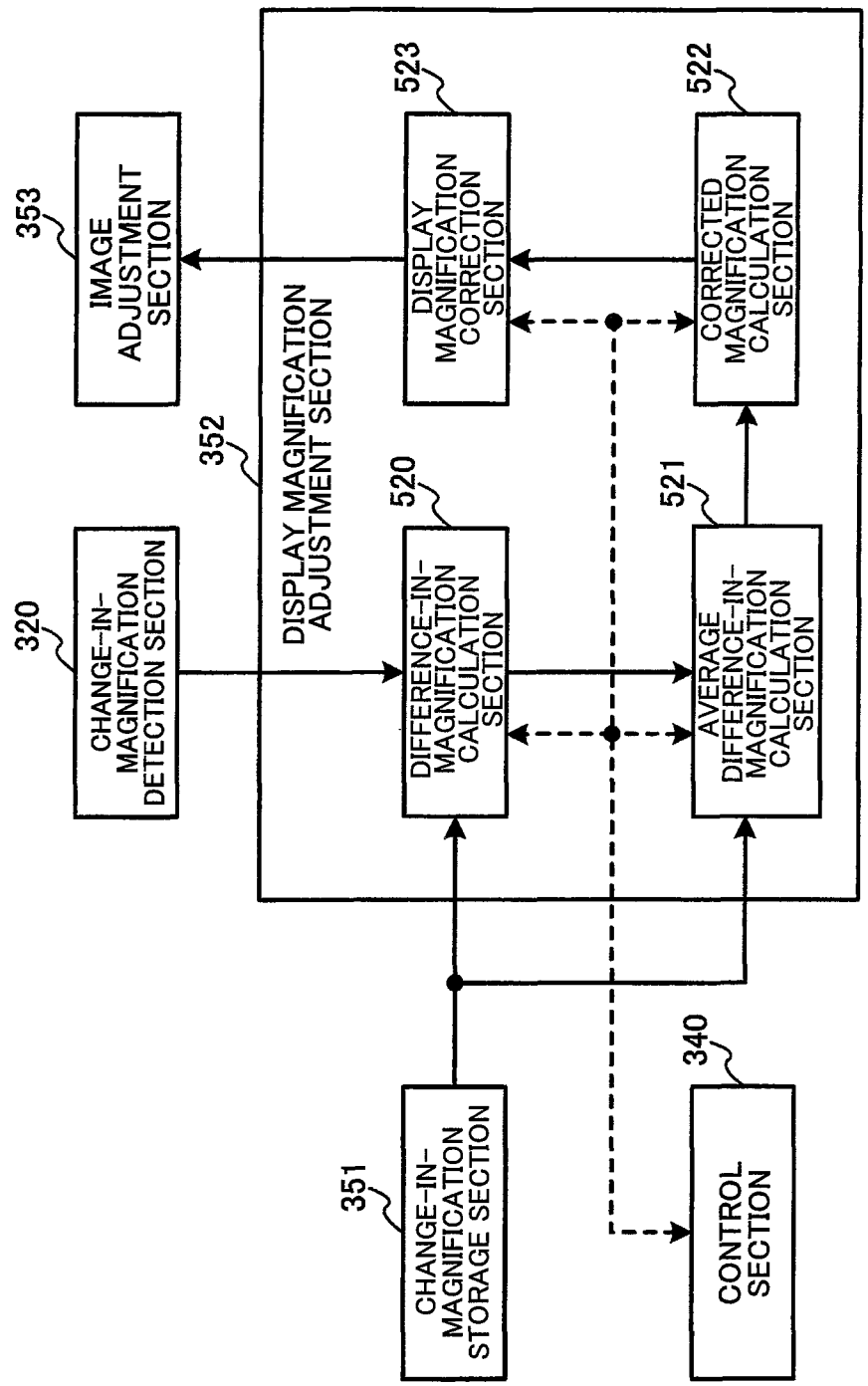
FIG. 22 illustrates a configuration example of a display magnification adjustment section according to the fourth embodiment.

The configuration of the display magnification adjustment section 352 according to the fourth embodiment is described below with reference to FIG. 22. The display magnification adjustment section 352 includes a difference-in-magnification calculation section 520, an average difference-in-magnification calculation section 521, a corrected magnification calculation section 522, and a display magnification correction section 523. The change-in-magnification detection section 320 is connected to the difference-in-magnification calculation section 520. The change-in-magnification storage section 351 is connected to the difference-in-magnification calculation section 520 and the average difference-in-magnification calculation section 521. The difference-in-magnification calculation section 520 is connected to the image adjustment section 353 through the average difference-in-magnification calculation section 521, the corrected magnification calculation section 522, and the display magnification correction section 523. The control section 340 is bidirectionally connected to the difference-in-magnification calculation section 520, the average difference-in-magnification calculation section 521, the corrected magnification calculation section 522, and the display magnification correction section 523, and controls the difference-in-magnification calculation section 520, the average difference-in-magnification calculation section 521, the corrected magnification calculation section 522, and the display magnification correction section 523 using a control signal.

The difference-in-magnification calculation section 520 calculates the difference between the change in magnification of the image corresponding to the current time output from the change-in-magnification detection section 320 and the change in magnification of the image in the preceding frame output from the change-in-magnification storage section 351 (see the following expression (7)), and outputs the calculation result to the average difference-in-magnification calculation section 521.

$$C[t]=Z[t]-Z[t-1] \quad (7)$$

where, t is the current time, Z[t] is the change in magnification of the image corresponding to the current time, Z[t−1] is the change in magnification of the image in the preceding frame, and C[t] is the difference in change in magnification at the current time. Note that the change in magnification Z[t] and the cumulative magnification A[t] are positive values, and the difference in change in magnification C[t] is a positive or negative value.

The average difference-in-magnification calculation section 521 calculates the average difference-in-magnification using the following expression (8), and outputs the calculation result to the corrected magnification calculation section 522.

$$AvC = \sum_{s}^{t} \frac{C[i]}{N} \quad (8)$$

where, t is the current time, s is the AF operation start time, AvC is the average difference in magnification, N is the number of images captured from the AF operation start time to the current time, and C[i] is the difference in change in magnification.

Figure 23:
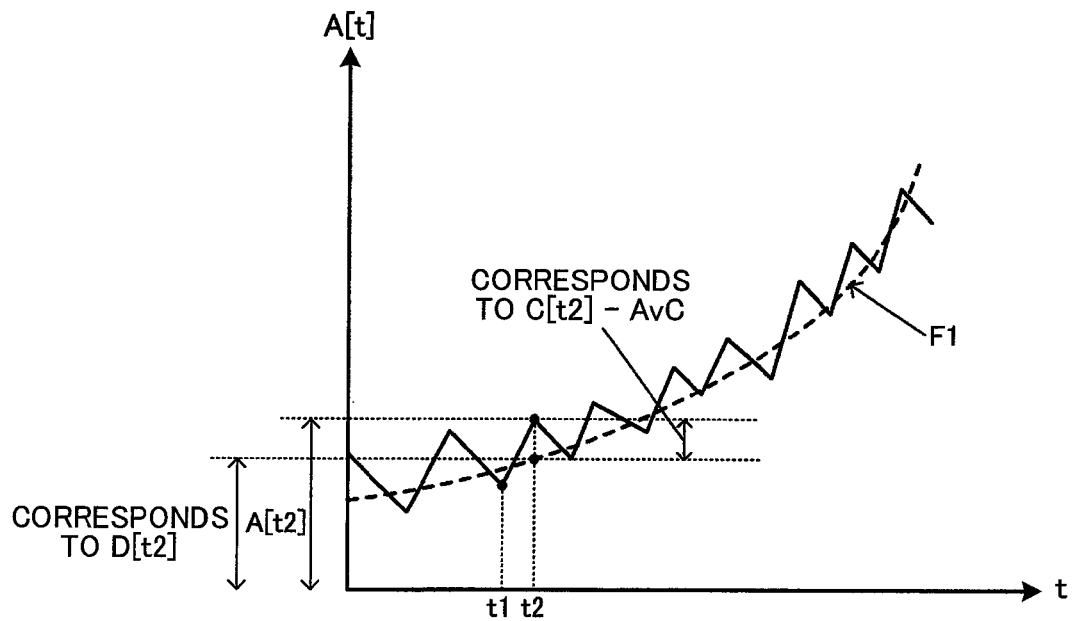
FIG. 23 illustrates an example of the detected change in magnification.

It was confirmed that the value D[t] calculated by the following expression (9) is a value obtained by removing (reducing in a broad sense) the high-frequency change-in-magnification component from the cumulative magnification A[t], and corresponds to F1 in FIG. 23, for example.

Therefore, the corrected magnification calculation section 522 calculates the change in magnification that excludes the high-frequency component due to wobbling using the expression (9), and outputs the calculation result to the display magnification correction section 523.

$$D[t]=A[t]-(C[t]-AvC) \quad (9)$$

where, t is the current time, A[t] is the cumulative magnification at the current time, C[t] is the difference in change in magnification at the current time, AvC is the average difference in magnification, and D[t] is the change in magnification that excludes the high-frequency component due to wobbling. FIG. 23 illustrates the above process using the timing t1 and the timing t2 as a specific example. Note that the values D[t] and E[t] (described later) correspond to a direct product of the magnification at the time t and the magnification at the preceding timing (corresponding to the ratio of the magnification at the time t and the magnification at a given reference timing). Therefore, the meaning of the values D[t] and E[t] is closer to that of the cumulative magnification A[t] than that of the change in magnification Z[t].

Figure 24:
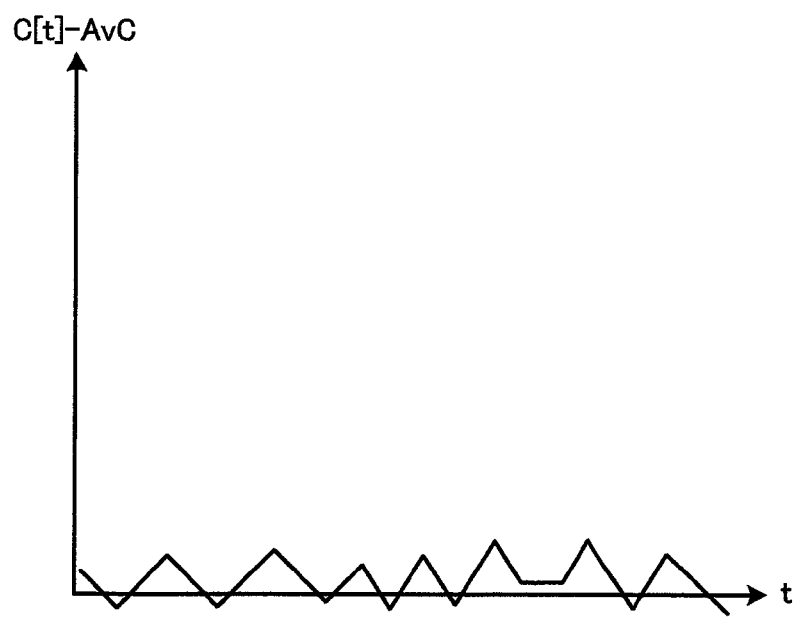
FIG. 24 illustrates an example of a change due to a high-frequency change in magnification relative to a low-frequency change in magnification.
Figure 25:
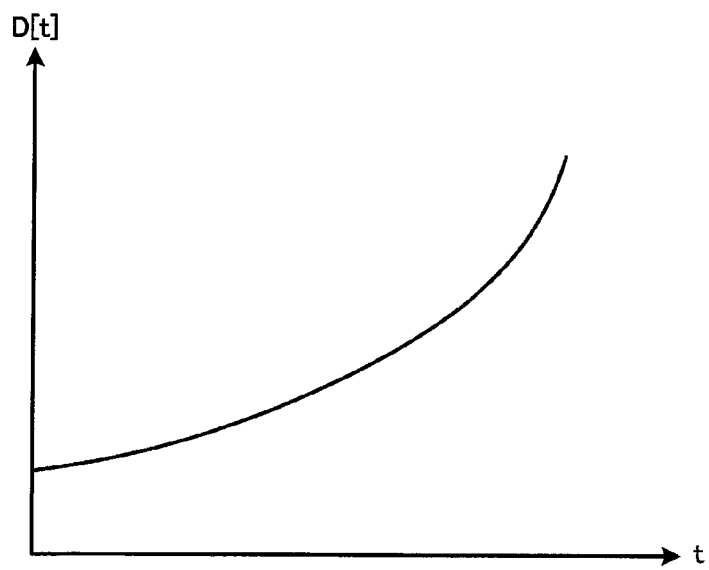
FIG. 25 illustrates an example in which the effects of a high-frequency component are reduced from the detected change in magnification.

FIG. 24 illustrates an example of a temporal change in the value "C[t]-AvC", and FIG. 25 illustrates an example of a temporal change in the value D[t]. It is desirable to reflect the change in magnification that corresponds to the value D[t] in the display image. Therefore, the value D[t] may be set as the target change in magnification, and the image scaling process may be performed so that the display image is scaled by a factor of D[t] relative to the reference magnification (e.g., the magnification at the start of the AF control process).

Specifically, the display magnification correction section 523 calculates a display magnification correction coefficient for correcting the display magnification using the following expression (10), and outputs the calculated display magnification correction coefficient to the image adjustment section 353.

$$E[t]=A[t]/D[t] \quad (10)$$

where, t is the current time, A[t] is the cumulative magnification at the current time, D[t] is the change in magnification that excludes the high-frequency component due to wobbling, and E[t] is the display magnification correction coefficient. Since the cumulative magnification A[t] includes both the high-frequency component and the low-frequency component, and the change in magnification D[t] excludes the high-frequency component (corresponding to the low-frequency component), the display magnification correction coefficient E[t] corresponds to the change in magnification that corresponds to the high-frequency component due to wobbling.

When the image scaling process using the cumulative magnification A[t] (e.g., a process using the value B[t]=1/A[t] (see the third embodiment) as a scaling coefficient) is performed on the image acquired by the image acquisition section 310, the low-frequency change in magnification that should be reflected in the display image is also corrected. This is because both the values D[t] and E[t] are used for the correction coefficient (see the expression (10)). Specifically, the desired display image can be generated by performing the image scaling process using the value E[t] obtained by the expression (10) (e.g., the image scaling process using the value "1/E[t]" as the scaling coefficient).

Therefore, the image adjustment section 353 adjusts the size of the image input from the image acquisition section

310 using the display magnification correction coefficient input from the display magnification correction section 523.

Figure 26:
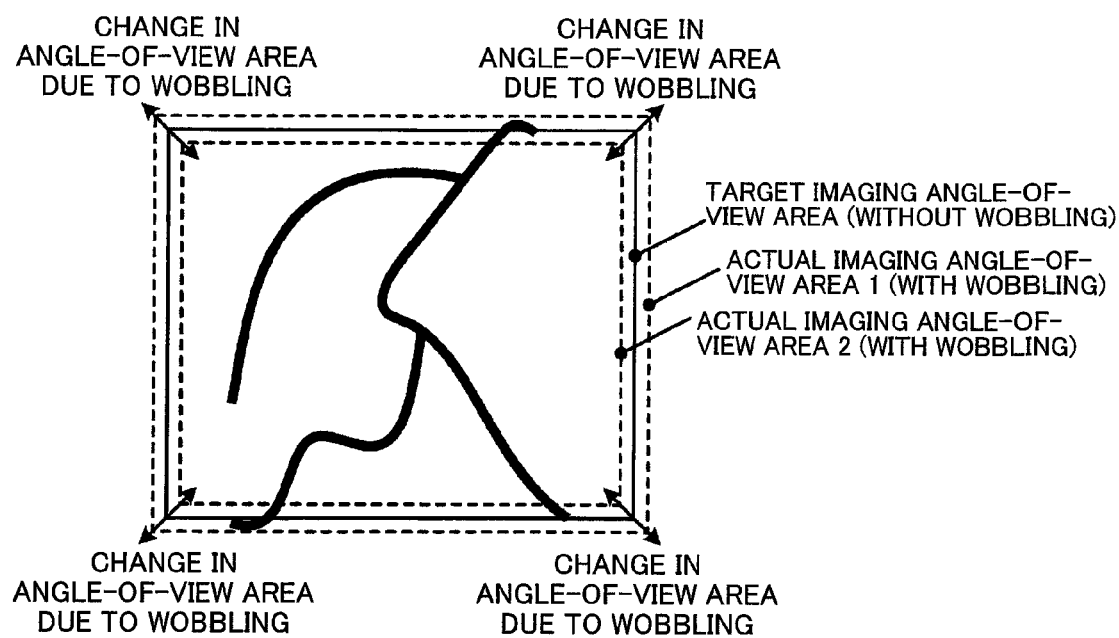
FIG. 26 is a view illustrating a change in angle-of-view area due to wobbling.

FIG. 26 illustrates a mechanism that adjusts the image size in order to correct the effects of wobbling. In FIG. 26, each angle-of-view area indicates the range of the captured object, and the size of the image that is captured by the imaging section 230 and acquired by the image acquisition section 310 is identical. Specifically, since the object over a wide range is included in the image having a given size when the angle-of-view area is large, a large angle-of-view area corresponds to a low magnification (demagnified state).

FIG. 26 illustrates an actual imaging angle-of-view area 1 (with wobbling), a target imaging angle-of-view area (without wobbling), and an actual imaging angle-of-view area 2 (with wobbling) in ascending order of the size of the imaging angle-of-view area. The actual imaging angle-of-view area 1 (with wobbling) corresponds to the imaging angle-of-view area when the objective lens 231 is positioned away from the object in the direction Z (vertical direction) as compared with the position of the objective lens 231 when wobbling is not performed. The actual imaging angle-of-view area 2 (with wobbling) corresponds to the imaging angle-of-view area when the objective lens 231 is positioned close to the object in the direction Z as compared with the position of the objective lens 231 when wobbling is not performed. The target imaging angle-of-view area (without wobbling) corresponds to the imaging angle-of-view area when wobbling is not performed. In the fourth embodiment, the image size is adjusted so that the range of the object included within the display image displayed on the display section 400 corresponds to (is identical with in a narrow sense) the target imaging angle-of-view area (without wobbling) even if the angle-of-view area has changed due to the effects of wobbling. This makes it possible to suppress the effects of wobbling on the display image. Since the size of the target imaging angle-of-view area (without wobbling) changes corresponding to a low-frequency change in magnification, the low-frequency change in magnification is not corrected when the target imaging angle-of-view area (without wobbling) is set as the target.

Figure 27:
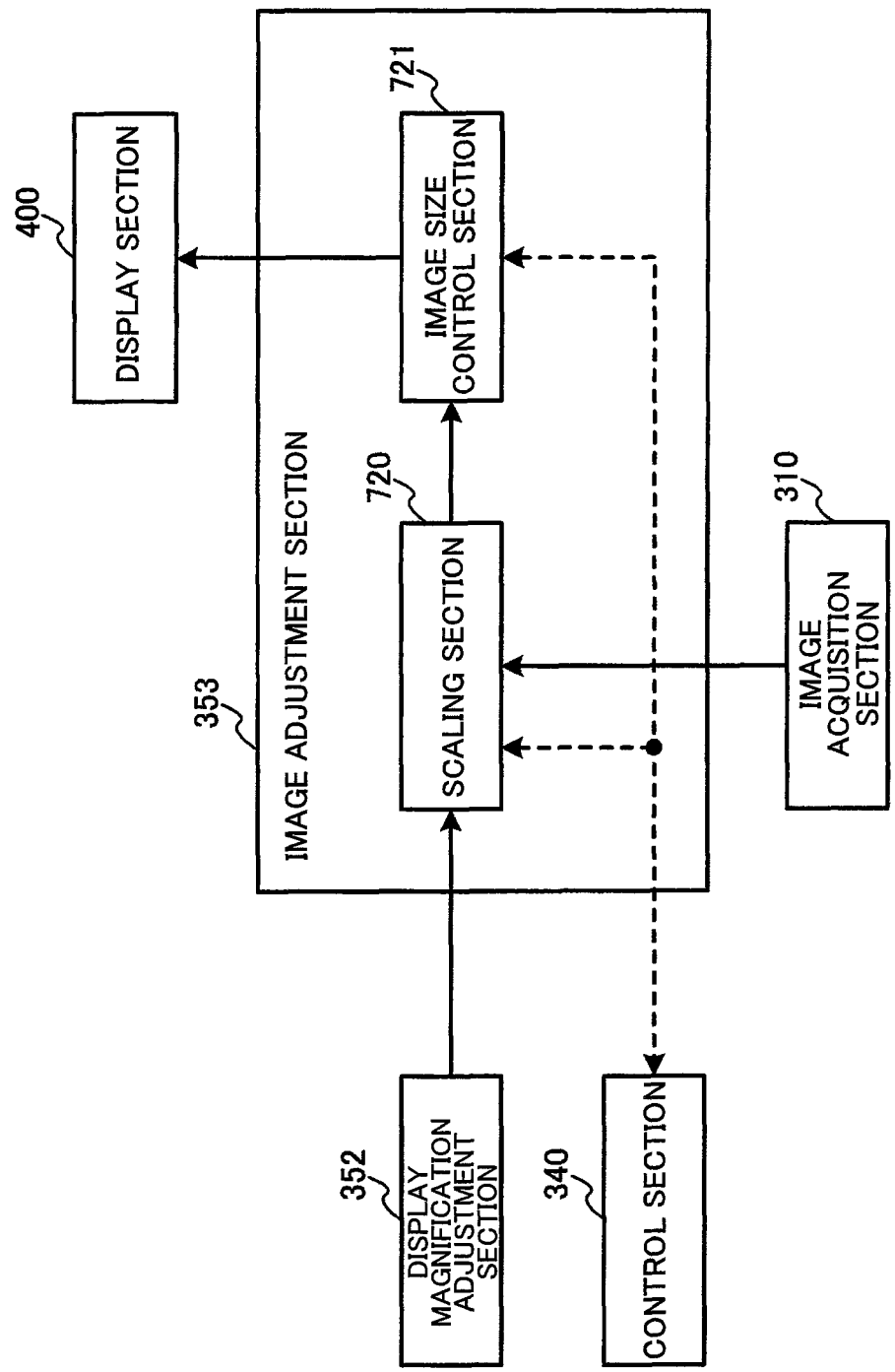
FIG. 27 illustrates a configuration example of an image adjustment section according to the fourth embodiment.

The configuration of the image adjustment section 353 according to the fourth embodiment is described below with reference to FIG. 27. The image adjustment section 353 includes a scaling section 720 and an image size control section 721. The display magnification adjustment section 352 is connected to the display section 400 through the scaling section 720 and the image size control section 721. The image acquisition section 310 is connected to the scaling section 720. The control section 340 is bidirectionally connected to the scaling section 720 and the image size control section 721, and controls the scaling section 720 and the image size control section 721 using a control signal.

The scaling section 720 performs a scaling process on the image (image width: imgWidth, image height: imgHeight) output from the image acquisition section 310 using the display magnification correction coefficient E[t] output from the display magnification adjustment section 352 under control of the control section 340.

When the imaging angle-of-view area is the actual imaging angle-of-view area 1 (with wobbling), the display magnification correction coefficient E[t] calculated by the expression (10) is smaller than 1 (i.e., the magnification is lower than the target magnification (i.e., the image has been demagnified)). Therefore, the size of the image output from the image acquisition section 310 is enlarged using a known interpolation technique.

When the imaging angle-of-view area is the actual imaging angle-of-view area 2 (with wobbling), the display magnification correction coefficient E[t] calculated by the expression (10) is larger than 1 (i.e., the magnification is higher than the target magnification (i.e., the image has been magnified)). Therefore, the size of the image output from the image acquisition section 310 is reduced using a known interpolation technique. The scaling section 720 outputs the image obtained by the scaling process to the image size control section 721.

Figure 28A:
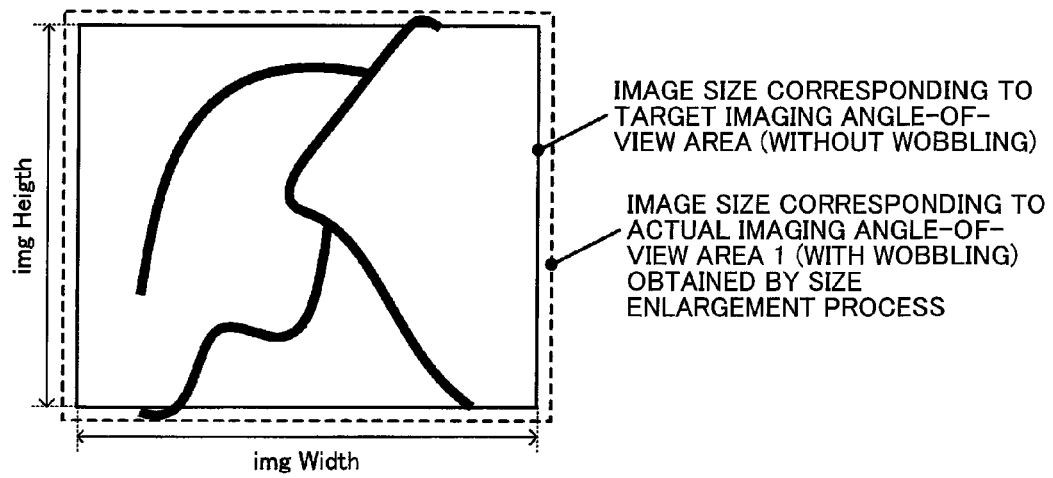
FIG. 28A illustrates an example in which a size enlargement process is performed as an image scaling process.
Figure 28B:
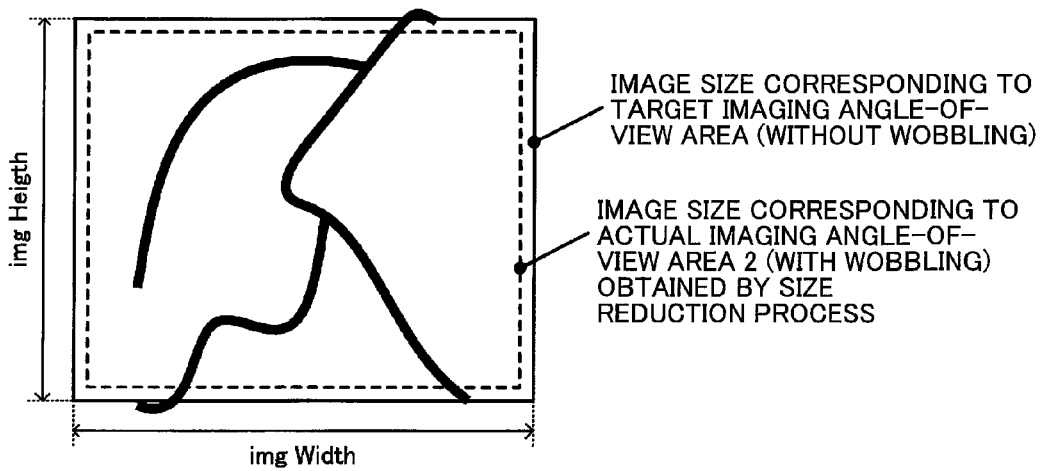
FIG. 28B illustrates an example in which a size reduction process is performed as an image scaling process.

The image size control section 721 performs an image size control process on the image output from the scaling section 720 under control of the control section 340 in order to display the image output from the scaling section 720 on the display section 400. FIGS. 28A and 28B illustrate a specific example of the image size control process. Note that FIGS. 28A and 28B illustrate the size of the scaled image obtained by performing the image scaling process on the image acquired by the image acquisition section 310. More specifically, FIGS. 28A and 28B illustrate the size of the scaled image obtained by performing the image scaling process so that the size of the object is identical in a virtual image when the target imaging angle-of-view area has been captured by the imaging section 230 and the image obtained by the image scaling process.

As illustrated in FIG. 28A, when the imaging angle-of-view area is the actual imaging angle-of-view area 1 (with wobbling), the size of the image obtained by the size enlargement process and output from the scaling section 720 is larger than the size (width: imgWidth, height: imgHeight) of the image acquired by the image acquisition section 310. Therefore, the image size control section 721 performs a crop process on the image output from the scaling section 720. Specifically, the image size control section 721 performs the crop process on the image output from the scaling section 720 so that the image is symmetrically cropped corresponding to the image size of the target imaging angle-of-view area around the center pixel in the vertical direction and the horizontal direction.

As illustrated in FIG. 28B, when the imaging angle-of-view area is the actual imaging angle-of-view area 2 (with wobbling), the size of the image obtained by the size reduction process and output from the scaling section 720 is smaller than the size (width: imgWidth, height: imgHeight) of the image acquired by the image acquisition section 310. Therefore, the image size control section 721 performs a peripheral interpolation process on the image output from the scaling section 720. Specifically, since the size of the image obtained by the size reduction process is smaller than the size of the target imaging angle-of-view area, the image size control section 721 performs an interpolation process on the image obtained by the size reduction process by symmetrically adding pixels to the peripheral area (i.e., the area enclosed by the broken line and the solid line in FIG. 28B) so that the image has the width imgWidth and the height imgHeight around the center pixel in the vertical direction and the horizontal direction. For example, the pixel value of each pixel situated in the peripheral area is set to a fixed value (e.g., 0). The image obtained by the interpolation process is output to the display section 400, and displayed on the display section 400.

Note that the image interpolation process may be implemented using various methods. For example, the image interpolation process may be implemented using a known mirror method, a copy method, or the like.

The high-frequency component due to wobbling can be reduced by thus adjusting the image size for detecting the change in magnification from the endoscopic image input from the image acquisition section 310, and displaying the endoscopic image.

Although a configuration example in which the image size is adjusted using the angle-of-view area without wobbling as the target imaging angle-of-view area has been described above, the configuration is not limited thereto. For example, the actual imaging angle-of-view area 2 (with wobbling) may be used as the target imaging angle-of-view area (modification).

For example, the display magnification correction section 523 may calculate the display magnification correction coefficient used for the image scaling process for removing the high-frequency component due to wobbling using the following expression (11) or (12), and output the calculated display magnification correction coefficient to the image adjustment section 353.

$$E'[t]=(A[t]*A[t])/(D[t]*D[t])*P1 \quad (11)$$

$$E'[t]=(A[t]*A[t])/(D[t]*D[t])+P2 \quad (12)$$

where, t is the current time, A[t] is the cumulative magnification at the current time, D[t] is the change in magnification that excludes the high-frequency component due to wobbling, E[t] is the display magnification correction coefficient, P1 is a constant, and P2 is a constant.

Figure 29:
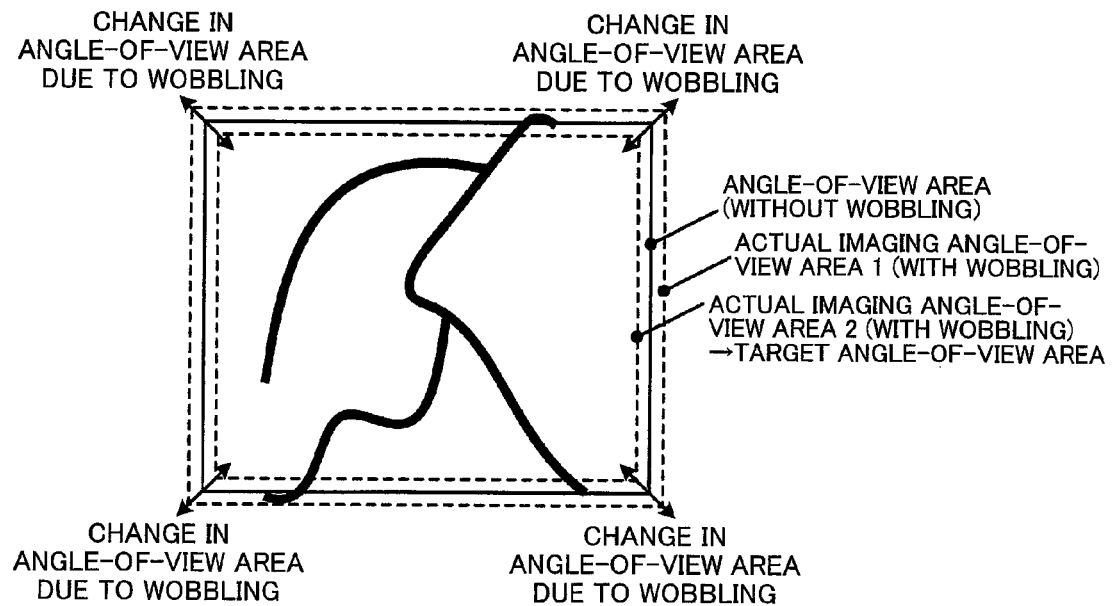
FIG. 29 is a view illustrating a target angle-of-view area according to a modification of the fourth embodiment.

When the image output from the image acquisition section 310 corresponds to the actual imaging angle-of-view area 2 (with wobbling) (target imaging angle-of-view area) (see FIG. 29), the scaling section 720 outputs the image to the image size control section 721 under control of the control section 340 without performing the scaling process on the image.

When the image output from the image acquisition section 310 corresponds to the actual imaging angle-of-view area 2 (with wobbling) (see FIG. 29), the scaling section 720 performs the size enlargement process on the image (image width: imgWidth, image height: imgHeight) output from the image acquisition section 310 using the display magnification correction coefficient E'[t] output from the display magnification adjustment section 352 under control of the control section 340 (e.g., the size of the image is enlarged by a factor of 1/E'[t]). The scaling section 720 outputs the image obtained by the scaling process to the image size control section 721.

The image size control section 721 performs the image size control process in the same manner as described above. In the above modification, the scaling section 720 performs the scaling (size enlargement) process only when the imaging angle-of-view area is the actual imaging angle-of-view area 1 (with wobbling) since the actual imaging angle-of-view area 2 is used as the target imaging angle-of-view area. Specifically, the image size control section 721 performs the image crop process at the timing corresponding to the actual imaging angle-of-view area 1, and outputs the resulting image to the display section 400. When the imaging angle-of-view area is the actual imaging angle-of-view area 2, the image size control section 721 outputs the image output from the scaling section 720 to the display section 400 without processing the image output from the scaling section 720.

Figure 30:
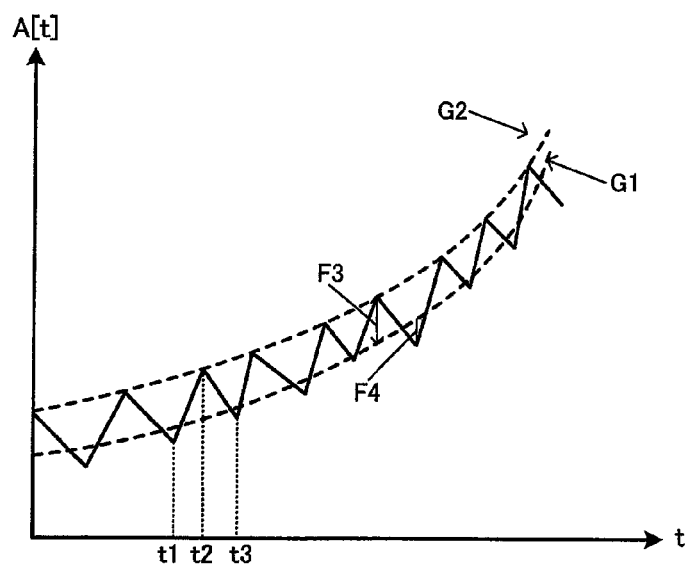
FIG. 30 is a view illustrating a process according to a modification of the fourth embodiment.

FIG. 30 illustrates the process according to the above modification. The process up to calculation of the value D[t] is performed in the same manner as in the example illustrated in FIG. 23. In the example illustrated in FIG. 23, the scaling process is performed using the value "A[t]/D[t]" (=E[t]) to increase the value at a point below the low-frequency change in magnification (G1) (e.g., the value at the time t1), and decrease the value at a point above the low-frequency change in magnification (G1) (e.g., the value at the time t2) so that the magnification of the display image in the processing target period approaches the low-frequency change in magnification (G1).

In the above modification, the low-frequency change in magnification (G1) is not used as a reference. Specifically, the value at a point below the low-frequency change in magnification (G1) is increased without changing the value at a point above the low-frequency change in magnification (G1) to correct the change in magnification in the processing target period to the low-frequency change in magnification (e.g., G2 in FIG. 30) that differs from the low-frequency change in magnification G1.

Specifically, since the upward change (e.g., F3 in FIG. 30) and the downward change (e.g., F4 in FIG. 30) due to the high-frequency change in magnification relative to the low-frequency change in magnification (G1) are corrected by the process based on the value "A[t]/D[t]", it is considered that the point corresponding to the downward change can be shifted upward to the point corresponding to the upward change (i.e., the point corresponding to G2) by performing the process based on the value "A[t]/D[t]" twice on the point corresponding to the downward change.

Specifically, a process using $\{A[t]/D[t]\}^2$ may be performed at the timing corresponding to the point corresponding to the downward change (e.g., t1 and t3) while skipping the process at the timing corresponding to the point corresponding to the upward change (e.g., t2). This corresponds to performing the image scaling process using the display magnification correction coefficient E'[t] in the expression (11) or (12) depending on the timing. When the value "A[t]/D[t]" has an error, the error may accumulate as a result of using the value "A[t]/D[t]" twice, and the accuracy of the image scaling process may deteriorate. Therefore, the coefficient P1 or P2 is used in the expression (11) or (12) taking account of an improvement in accuracy and the like.

Since the process performed by the scaling section 720 is limited to the size enlargement process when using the method according to the modification, the control process performed by the image size control section 721 can be limited to the crop process. Since the interpolation process is performed by the image size control section 721 when the size reduction process is performed by the scaling section 720, useful information may not be acquired in the peripheral area (a fixed value is used). However, such a problem does not occur when using the method according to the modification.

However, since it is necessary to classify the timings into a timing at which the image scaling process using the display magnification correction coefficient E'[t] is performed and a timing at which the image scaling process using the display magnification correction coefficient E'[t] is not performed, it is necessary for the image scaling section to appropriately determine whether or not to perform the image scaling process at the processing target timing. For example, when the timings t1, t2, and t3 in FIG. 30 are adjacent timings (i.e., when the image is acquired corresponding to a change due to wobbling), the image scaling process may be performed every other timing except for the case where the image cannot be acquired, for example.

Figure 20:
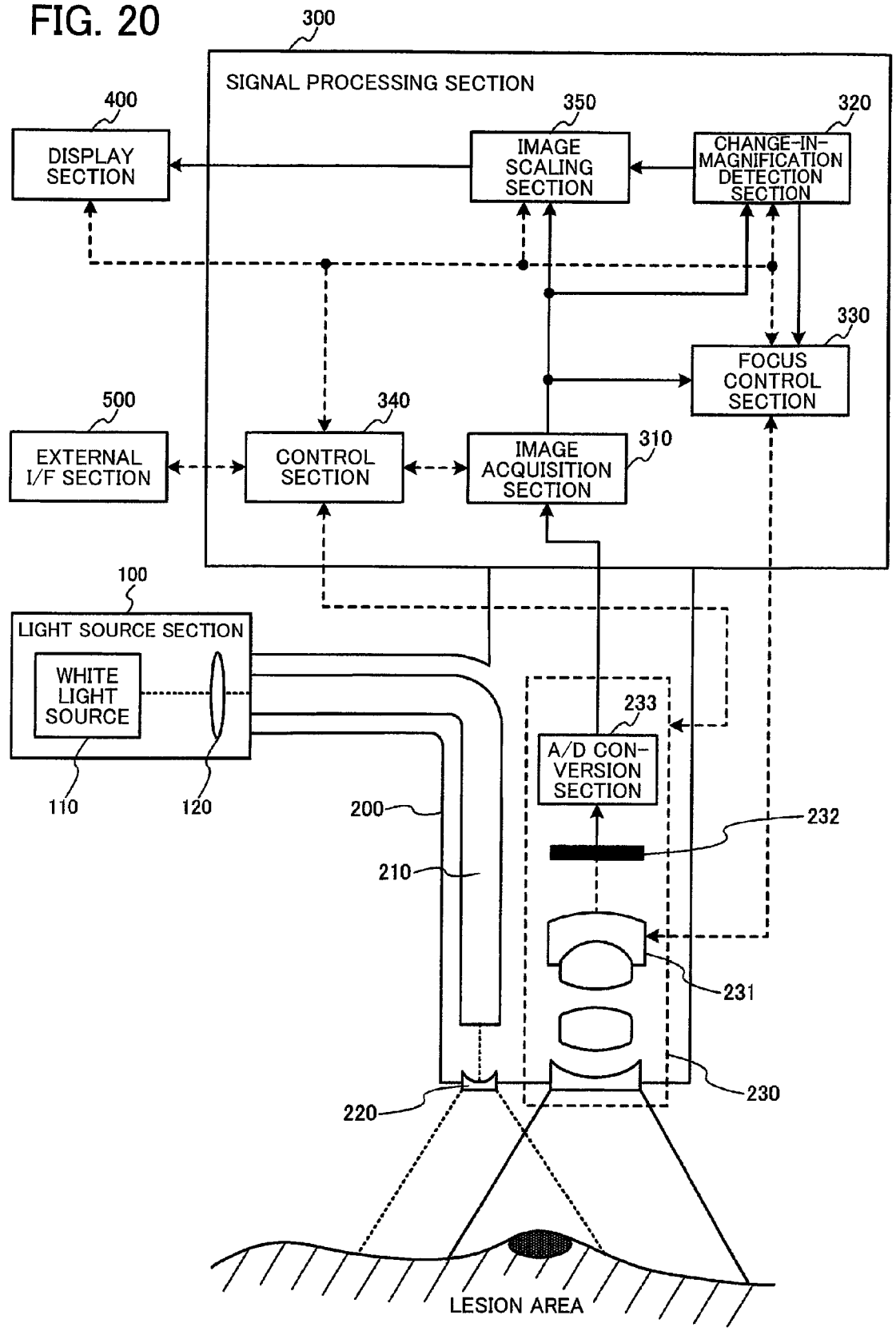
FIG. 20 illustrates a configuration example of a focus control device according to a fourth embodiment and an endoscope system including the same.

According to the fourth embodiment, the focus control device includes the image scaling section 350 that subjects the image to the image scaling process to acquire the display image that is displayed on the display section 400 (see FIG. 20). The image scaling section 350 calculates a global change in magnification included in the detected change in magnification as a target change in magnification, and performs the image scaling process based on the calculated target change in magnification.

The term "global" used herein forms a counterpart to the term "local", and is used to refer to a relatively wide range. Therefore, the global change in magnification refers to the change in magnification in a wide range when the change in magnification is classified into the change in magnification in a wide range and the change in magnification in a narrow range (local change in magnification). The term "range" used herein in connection with the change in magnification may be a time span, or may be the degree of change in the value. In the example illustrated in FIG. 23, the change in magnification indicated by the solid line can be divided into the element illustrated in FIG. 24 and the element illustrated in FIG. 25. Since the change in value in the vertical axis direction is small in FIG. 24, and the change in value in the vertical axis direction is larger in FIG. 25 as compared with FIG. 24, the value D[t] illustrated in FIG. 25 may be considered to be the global change in magnification. When the value changes cyclically in FIGS. 24 and 25, the length of one cycle may be taken into consideration. In FIG. 24, the cycle is short since the value frequently changes in the vertical direction. In FIG. 25, it is considered that the cycle is very long since the value does not change cyclically within the range illustrated in FIG. 25. Specifically, the change in the value in FIG. 24 corresponds to the local change in magnification, and the change in the value D[t] in FIG. 25 corresponds to the global change in magnification when the time-axis range is taken into consideration. In other words, when the change in magnification is divided into the high-frequency change in magnification and the low-frequency change in magnification, the low-frequency change in magnification is considered to be an example of the global change in magnification.

According to the above configuration, since the display image acquired by an appropriate image scaling process can be displayed on the display section 400, it is possible to present an image that is easy to observe to the user, for example. In particular, when the low-frequency change in magnification is considered to be the global change in magnification, the element (high-frequency change in magnification) of the change in magnification other than the global change in magnification may frequently change the angle of view of the display image, and may significantly impair the observability of the image for the user. It is possible to suppress such a problem by utilizing the global change in magnification as the target.

According to the fourth embodiment, the focus control device includes the image scaling section 350 that subjects the image to the image scaling process to acquire the display image that is displayed on the display section 400 (see FIG. 20). The image scaling section 350 calculates the detected change in magnification that excludes a change in magnification due to the driving of the imaging optical system for focus control as the target change in magnification, and performs the image scaling process based on the target change in magnification to cancel a change in angle of view due to the driving of the imaging optical system for focus control.

The imaging optical system may be driven for focus control when performing wobbling for implementing the contrast AF operation. It is normally convenient to the user when the time required for the AF operation is as short as possible. Therefore, it is considered that the imaging optical system (zoom lens in a narrow sense) is driven at a high speed during wobbling, and the change in magnification due to the imaging optical system driven during wobbling occurs at a very high frequency as compared with a change in magnification due to other factors.

According to the above configuration, since the display image can be acquired using the change in magnification that excludes a high-frequency change in magnification due to wobbling or the like as the target change in magnification, it is possible to present an image that is easy to observe to the user, for example. Specifically, FIG. 23 illustrates the detected change in magnification, FIG. 24 illustrates the change in magnification due to wobbling, and FIG. 25 illustrates the change in magnification (target change in magnification) that excludes the effects of wobbling. When using the method according to the fourth embodiment, it is possible to suppress a situation in which the display image becomes difficult to observe due to the effects of wobbling while allowing the change in magnification (FIG. 25) due to other factors to be reflected in the display image. Specifically, when the user has changed the imaging magnification, or brought the imaging section 230 close to the object, for example, the user can determine the results thereof from a change in the display image.

Note that the global change in magnification or the change in magnification that excludes a change in magnification due to the driving of the imaging optical system for focus control is not limited to FIG. 25 (F1 in FIG. 23 or G1 in FIG. 30), but may be G2 in FIG. 30 (see the modification).

The image scaling section 350 may include the difference-in-magnification calculation section 520 that calculates change-in-magnification difference information, the change-in-magnification difference information being information about the difference in the change in magnification between a first timing and a second timing that differs from the first timing, and the average difference-in-magnification calculation section 521 that calculates average magnification difference information that indicates the average value of the change-in-magnification difference information. The image scaling section 350 may calculate the target change in magnification based on the detected change in magnification, the change-in-magnification difference information, and the average magnification difference information.

The change-in-magnification difference information may be C[t] (see above), and the average magnification difference information may be AvC (see above).

The above configuration makes it possible to calculate the target change in magnification based on the change-in-magnification difference information and the average magnification difference information. Specifically, the target change in magnification D[t] may be calculated by the expression (9) using the change in magnification (particularly the cumulative magnification A[t]), C[t], and AvC.

The image scaling section 350 may calculate an image scaling coefficient based on the detected change in magnification and the target change in magnification, and perform the image scaling process using the calculated image scaling coefficient. The image scaling section 350 may subject the image to the scaling process using the image scaling coefficient to acquire the display image.

The above configuration makes it possible to calculate the image scaling coefficient, and perform the image scaling process based on the calculated image scaling coefficient. The target change in magnification D[t] means that it is possible to present an image that is easy to observe to the user by utilizing the image scaled by a factor of D[t] relative to the reference magnification as the display image. The image acquired by the image acquisition section 310 has been scaled by a factor of A[t] (=D[t]×E[t]), and an unnecessary change in magnification is added by E[t]. Specifically, it is necessary to perform a process that calculates E[t] from A[t] and D[t] instead of D[t] in order to meet the target. This process corresponds to a process that solves the expression (10). The actual image scaling process may include a process that cancels unnecessary E[t]. This process may be an image scaling process that multiplies 1/E[t] as a coefficient, for example.

The change-in-magnification detection section 320 may detect the change in the size of the object within the image as the change in magnification. The image scaling section 350 may calculate the target change in magnification based on the change in magnification that is the change in the size of the object.

The above configuration makes it possible to use the method according to the fourth embodiment even when detecting the change in the size of the object as the change in magnification (particularly when the change in the imaging magnification is not acquired from the control signal or the like). When detecting the change in the size of the object as the change in magnification, a change is also reflected in the change in magnification when the distance between the imaging section 230 and the object has changed. Specifically, when the detected change in magnification is used directly for the image scaling process on the display image, the size of the object may not change within the display image even when the distance between the imaging section 230 and the object has changed. In this case, it may be difficult for the user to determine the distance to the object, and the imaging section 230 may collide with the object. In particular, tissue may be damaged (i.e., it is very dangerous) when using an endoscope system as the focus control device. Therefore, the method according to the fourth embodiment is advantageous when detecting the change in the size of the object as the change in magnification.

The focus control device and the like according to the embodiments of the invention may include a processor and a memory. The processor may be a central processing unit (CPU), for example. Note that the processor is not limited to a CPU. Various types of processors such as a graphics processing unit (GPU) and a digital signal processor (DSP) may also be used. The processor may be a hardware circuit that includes an application specific integrated circuit (ASICA. The memory stores a computer-readable instruction. Each section of the focus control device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set of a program, or may be an instruction that causes a hardware circuit of the processor to operate.

The first to fourth embodiments according to the invention and the modifications thereof have been described above. Note that the invention is not limited to the first to fourth embodiments and the modifications thereof. Various modifications and variations may be made of the first to fourth embodiments and the modifications thereof without departing from the scope of the invention. A plurality of elements described in connection with the first to fourth embodiments and the modifications thereof may be appropriately combined to implement various configurations. For example, an arbitrary element may be omitted from the elements described in connection with the first to fourth embodiments and the modifications thereof. Arbitrary elements among the elements described in connection with the first to fourth embodiments and the modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. A focus control device comprising:
a focus control section that controls an imaging optical system that is configured so that an in-focus object plane position is changed when an imaging magnification is changed;
an image acquisition section that acquires a plurality of images captured through the imaging optical system at a different imaging magnification;
a change-in-magnification detection section that detects a change in magnification, the change in magnification being at least one of a change in the imaging magnification and a change in size of an object within an image among the plurality of images; and
an image scaling section that subjects the image to an image scaling process based on the change in magnification to acquire a scaled image,
the focus control section calculating an autofocus (AF) evaluation value that indicates a focus state of the imaging optical system based on the image and the change in magnification, and driving the imaging optical system based on the calculated AF evaluation value to control focus of the imaging optical system, and
the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

2. The focus control device as defined in claim 1,
the image scaling section acquiring the scaled image having a relatively small size when the change in magnification is relatively large, and acquiring the scaled image having a relatively large size when the change in magnification is relatively small.

3. The focus control device as defined in claim 2,
the change-in-magnification detection section detecting the change in magnification between a first timing and a second timing that differs from the first timing, and
the image scaling section subjecting the image acquired by the image acquisition section at the second timing to the image scaling process using a reciprocal of the change in magnification to acquire the scaled image.

4. The focus control device as defined in claim 1,
the image scaling section outputting the acquired scaled image to the focus control section and a display device.

5. The focus control device as defined in claim 4,
the image scaling section outputting a first scaled image obtained by subjecting the image to a first image scaling process to the focus control section, and outputting a second scaled image obtained by subjecting the image to a second image scaling process that differs from the first image scaling process to the display device.

6. The focus control device as defined in claim 5,
the change-in-magnification detection section detecting a first change in magnification and a second change in magnification as the change in magnification, the first change in magnification being the change in the size of the object within the image, and the second change in magnification being the change in the imaging magnification, and the image scaling section performing the first image scaling process based on the first change in magnification to acquire the first scaled image, and performing the second image scaling process based on the second change in magnification to acquire the second scaled image.

7. The focus control device as defined in claim 5,
the image scaling section performing the image scaling process in a period from a first timing to an Nth timing (N is an integer equal to or larger than 2),
the change-in-magnification detection section detecting an ith ($1 \leq i \leq N$) change in magnification at an ith timing, and
the image scaling section performing the second image scaling process at a kth ($1 \leq k \leq N$) timing based on a first change in magnification to a kth change in magnification to acquire the second scaled image, and outputting the second scaled image to the display device.

8. The focus control device as defined in claim 5,
the image scaling section performing the image scaling process in a period from a first timing to an Nth timing (N is an integer equal to or larger than 2),
the change-in-magnification detection section detecting an ith ($1 \leq i \leq N$) change in magnification at an ith timing, and
the image scaling section determining whether or not the change in magnification at an mth ($1 \leq m \leq N$) timing is included within a given allowable scaling range, performing the second image scaling process at the mth timing in a way similar to the second image scaling process at an (m−1)th timing that precedes the mth timing when the change in magnification at the mth timing is included within the given allowable scaling range, and performing the second image scaling process at the mth timing using a value closer to 1 than a reciprocal of an mth change in magnification when the change in magnification at the mth timing is not included within the given allowable scaling range.

9. The focus control device as defined in claim 1,
the change-in-magnification detection section detecting a ratio of a magnification evaluation value at a second timing to the magnification evaluation value at a first timing as the change in magnification at the second timing, the second timing differing from the first timing, and the magnification evaluation value being at least one of the imaging magnification and the size of the object within the image.

10. The focus control device as defined in claim 9,
the change-in-magnification detection section detecting a ratio of the imaging magnification at a second timing to the imaging magnification at a first timing as the change in magnification at the second timing, the second timing differing from the first timing.

11. The focus control device as defined in claim 9,
the change-in-magnification detection section detecting a ratio of the size of the object at a second timing to the size of the object at a first timing as the change in magnification at the second timing, the second timing differing from the first timing.

12. The focus control device as defined in claim 11,
the change-in-magnification detection section detecting the change in magnification by applying a phase-only correlation technique to the image at the first timing and the image at the second timing.

13. The focus control device as defined in claim 11,
the change-in-magnification detection section setting a plurality of feature points to the image at the first timing and the image at the second timing, and detecting the change in magnification based on positions of the plurality of feature points.

14. The focus control device as defined in claim 9,
the first timing being a timing at which the AF evaluation value starts to be calculated.

15. The focus control device as defined in claim 9,
the first timing and the second timing being adjacent AF evaluation value acquisition timings.

16. The focus control device as defined in claim 1,
the change-in-magnification detection section including a change-in-distance detection section that detects a change in distance information about a distance from the imaging optical system to the object, and
the change-in-distance detection section detecting the change in the distance information based on the change in the imaging magnification and the change in the size of the object.

17. The focus control device as defined in claim 1,
the image scaling section calculating a global change in magnification included in the detected change in magnification as the target change in magnification, and performing the image scaling process based on the calculated target change in magnification.

18. The focus control device as defined in claim 1,
the image scaling section including:
a difference-in-magnification calculation section that calculates change-in-magnification difference information, the change-in-magnification difference information being information about a difference in the change in magnification between a first timing and a second timing that differs from the first timing; and
an average difference-in-magnification calculation section that calculates average magnification difference information that indicates an average value of the change-in-magnification difference information, and
the image scaling section calculating the target change in magnification based on the detected change in magnification, the change-in-magnification difference information, and the average magnification difference information.

19. The focus control device as defined in claim 18,
the image scaling section calculating an image scaling coefficient based on the detected change in magnification and the target change in magnification, and performing the image scaling process using the calculated image scaling coefficient.

20. The focus control device as defined in claim 19,
the image scaling section subjecting the image to a scaling process using the image scaling coefficient to acquire a display image.

21. The focus control device as defined in claim 17,
the image scaling section including:
a difference-in-magnification calculation section that calculates change-in-magnification difference information, the change-in-magnification difference information being information about a difference in the change in magnification between a first timing and a second timing that differs from the first timing; and
an average difference-in-magnification calculation section that calculates average magnification difference information that indicates an average value of the change-in-magnification difference information, and the image scaling section calculating the target change in magnification based on the detected change in magnification, the change-in-magnification difference information, and the average magnification difference information.

22. The focus control device as defined in claim 21, the image scaling section calculating an image scaling coefficient based on the detected change in magnification and the target change in magnification, and performing the image scaling process using the calculated image scaling coefficient.

23. The focus control device as defined in claim 22, the image scaling section subjecting the image to a scaling process using the image scaling coefficient to acquire a display image.

24. The focus control device as defined in claim 1, the change-in-magnification detection section detecting the change in the size of the object within the image as the change in magnification, and the image scaling section calculating the target change in magnification based on the change in magnification that is the change in the size of the object.

25. An endoscope system comprising:

a focus control section that controls an imaging optical system that is configured so that an in-focus object plane position is changed when an imaging magnification is changed;

an image acquisition section that acquires a plurality of images captured through the imaging optical system at a different imaging magnification;

a change-in-magnification detection section that detects a change in magnification, the change in magnification being at least one of a change in the imaging magnification and a change in size of an object within an image among the plurality of images; and an image scaling section that subjects the image to an image scaling process based on the change in magnification to acquire a scaled image, the focus control section calculating an autofocus (AF) evaluation value that indicates a focus state of the imaging optical system based on the image and the change in magnification, and driving the imaging optical system based on the calculated AF evaluation value to control focus of the imaging optical system, and the image scaling section calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

26. A focus control method that controls an imaging optical system that is configured so that an in-focus object plane position is changed when an imaging magnification is changed, the focus control method comprising:

acquiring a plurality of images captured through the imaging optical system at a different imaging magnification;

detecting a change in magnification that is at least one of a change in the imaging magnification and a change in size of an object within an image among the plurality of images;

subjecting the image to an image scaling process based on the change in magnification to acquire a scaled image;

calculating an autofocus (AF) evaluation value that indicates a focus state of the imaging optical system based on the acquired image and the change in magnification, and driving the imaging optical system based on the calculated AF evaluation value to control focus of the imaging optical system; and calculating the detected change in magnification that excludes a change in magnification due to the driving of the imaging optical system for focus control as a target change in magnification, and performing the image scaling process based on the target change in magnification to cancel a change in angle of view due to the driving of the imaging optical system for focus control.

* * * * *